(12) United States Patent
Famodu et al.

(10) Patent No.: US 6,696,619 B1
(45) Date of Patent: Feb. 24, 2004

(54) PLANT AMINOACYL-TRNA SYNTHETASES

(76) Inventors: Omolayo O. Famodu, 216 Barrett Run Pl., Newark, DE (US) 19702; Carl Simmons, 4228 Holland Dr., Des Moines, IA (US) 50310

( * ) Notice: Subject to any disclaimer, the term of this patent is extended or adjusted under 35 U.S.C. 154(b) by 0 days.

(21) Appl. No.: 09/436,699

(22) Filed: Nov. 4, 1999

Related U.S. Application Data

(60) Provisional application No. 60/107,276, filed on Nov. 5, 1998.

(51) Int. Cl.[7] .......................... A01H 3/00; C07H 21/04; C07K 14/415; C12N 5/14; C12N 9/00
(52) U.S. Cl. .......................... 800/278; 435/6; 435/69.1; 435/183; 435/410; 435/419; 435/252.3; 435/320.1; 530/370; 536/23.1; 536/23.2; 536/23.6; 536/24.1; 536/24.3; 536/24.33; 536/24.5; 800/295
(58) Field of Search .......................... 435/6, 69.1, 183, 435/410, 419, 252.3, 320.1; 530/370; 536/23.1, 23.2, 23.6, 24.1, 24.3, 24.33, 24.5; 800/278, 295

(56) References Cited

U.S. PATENT DOCUMENTS 5,349,123 A * 9/1994 Shewmaker et al.

OTHER PUBLICATIONS

Bork, P. Genome Research, vol. 10, p. 398–400, 2000.*
Wolfgang Freist et al., Threonyl–tRNA Synthetase, Biol. Chem. Hoppe–Seyler, vol. 376, pp 213–224, Apr. 1995.
Neidhart et al., (1975) Annu. Rev. Microbiol. 29:215–250.
Eriani et al. (1990) Nature 347:203–206.
Lloyd et al., (1995) Nucleic Acid Research 23(15):2882–2892.
NCBI General Identifier No. 3319776.
NCBI General Identifier No. 2501056.
NCBI General Identifier No. 3617770.
Plant Physiol. 121, 1053–1055 (1999) Nykiforuk et al.
Ovesna et al., Plant Mitochondria, From Gene to Function: 139–142 (1998).
Weygand–Durasevic, Nucleic Acid Research 15(5), 1887–1904 (1987) (Medline 87174725).
Pape et al., Nucleic Acid Research 13(17), 6171–6183 (1985) (Medline 86016080).

* cited by examiner

*Primary Examiner*—Phuong T. Bui

(57) ABSTRACT

This invention relates to an isolated nucleic acid fragment encoding an aminoacyl-tRNA synthetase. The invention also relates to the construction of a chimeric gene encoding all or a portion of the aminoacyl-tRNA synthetase, in sense or antisense orientation, wherein expression of the chimeric gene results in production of altered levels of the aminoacyl-tRNA synthetase in a transformed host cell.

14 Claims, No Drawings

PLANT AMINOACYL-TRNA SYNTHETASES

This application claims priority benefit of U.S. Provisional Application No. 60/107,276 filed Nov. 5, 1998, now pending.

FIELD OF THE INVENTION

This invention is in the field of plant molecular biology. More specifically, this invention pertains to nucleic acid fragments encoding aminoacyl-tRNA synthetases in plants and seeds.

BACKGROUND OF THE INVENTION

Aminoacyl-tRNA Synthetases (AARS) are enzymes that charge (acylate) tRNAs with amino acids. These charged aminoacyl tRNAs then participate in mRNA translation and protein synthesis. The AARS show high specificity for charging a specific tRNA with the appropriate amino acid, for example valyl-tRNA with valine by valyl-tRNA synthetase or tryptophanyl-tRNA with tryptophan by tryptophanyl-tRNA synthetase. In general, per organism there are at least one AARS for each of the twenty amino acids. There are exceptions however. AARS are ancient enzymes, having functioned in translation since early life evolution. Some have speculated that the earliest aminoacyl-tRNA synthetases were mRNAs, not proteins, with the proteinaceous AARS described here emerging later (Neidhardt et al., (1975) *Annu. Rev. Microbiol.* 29:215–250). AARS are structurally diverse, although AARSs for some amino acids are more closely related than for others. AARSs are generally divided into two classes, class I and class II based on structural similarity and amino acid preferences (Eriani et al., (1990) *Nature* 347:203–206).

Plants like all other cellular organisms have aminoacyl-tRNA synthetases. However, a full description of the plant 'complement' of aminoacyl-tRNA synthetases has not yet been described. Full-length cDNA, genomic clones, and EST sequences for a variety of plant aminoacyl-tRNA synthetases are known. However, several anticipated aminoacyl-tRNA synthetases have not been discovered.

Because of the central role of protein synthesis in life, any agent that inhibits or disrupts this activity is likely to be toxic. Aminoacyl-tRNA synthetases play a critical role in protein translation by linking genetic nucleic acid information to protein synthesis. Aminoacyl-tRNA synthetases perform this role by "reading" the identity of the different tRNAs and acylating them with the correct cognate amino acid. A large volume of research over several decades has been focused on identifying inhibitors of this process. Inhibitors of aminoacyl-tRNA synthetases have been found to be cytotoxic due to their inhibition of protein synthesis. As such they therefore could be used as herbicides or in aminoacyl-tRNA synthetase selectable marker systems (Lloyd et al., (1995) *Nucleic Acid Research* 23(15):2882–2892). The genes disclosed herein can serve as the basis for testing whether the encoded aminoacyl-tRNA synthetases are sensitive to known inhibitors or other chemicals.

Biochemical processes are often compartmentalized in regions of cells, such as mitochondria, plastids, and lysosomes. These organelles are key sites for many biochemical pathways. Bioengineering of these processes may require targeting protein products to specific organells. One method to accomplish this involves the addition of an N-terminal prosequence (transit peptide) that directs protein entry into a specific organelle(s). Upon or shortly after transport into the organelle the transit peptide is usually proteolytically removed, and the mature protein is then able to function.

A few plant transit peptides have been shown empirically to be capable of directing fused proteins into specific organelles. However this ability appears to depend upon the structure of the protein being imported and to date it is impossible to predict whether a protein will be imported into an organelle with a given transit peptide. As such, it is advantageous to have a diversity of potential transit peptides from which the most efficient candidate can be chosen to target a protein of interest to an organelle. A number of plant transit peptides are known which direct mature proteins to mitochondria or chloroplast organells. These transit peptides are diverse in structure (length and amino acid sequence) and there is no strong consensus sequence identifying them. In addition, there is no obvious clear relationship between chloroplast targeting and mitochondrial targeting transit sequences. This invention describes a number of chloroplast-targeting and mitochondria-targeting transit peptides for (maize) aminoacyl-tRNA synthetases. These sequences will find utility in directing both aminoacyl-tRNA synthetase and other proteins into these organelles.

Accordingly, the availability of nucleic acid sequences encoding all or a portion of these enzymes would facilitate studies to better understand protein synthesis in plants, provide genetic tools for the manipulation of gene expression, protein targeting to specific organells and provide possible targets for herbicides.

SUMMARY OF THE INVENTION

The present invention relates to isolated polynucleotides comprising a nucleotide sequence encoding a first polypeptide of at least 116 amino acids that has at least 85% identity based on the Clustal method of alignment when compared to a polypeptide selected from the group consisting of a rice seryl-tRNA synthetase polypeptide of SEQ ID NO:16, a soybean seryl-tRNA synthetase polypeptide of SEQ ID NO:18, or a wheat seryl-tRNA synthetase polypeptide of SEQ ID NO:20. The present invention also relates to an isolated polynucleotide comprising the complement of the nucleotide sequences described above.

The present invention also relates to isolated polynucleotides comprising a nucleotide sequence encoding a second polypeptide of at least 483 amino acids that has at least 80% identity based on the Clustal method of alignment when compared to a polypeptide selected from the group consisting of a corn threonyl-tRNA synthetase polypeptide of SEQ ID NO:22, a rice threonyl-tRNA synthetase polypeptide of SEQ ID NO:24, a soybean threonyl-tRNA synthetase polypeptide of SEQ ID NO:26, or a wheat threonyl-tRNA synthetase polypeptide of SEQ ID NO:28. The present invention also relates to an isolated polynucleotide comprising the complement of the nucleotide sequences described above.

The present invention relates to an isolated polynucleotide comprising a nucleotide sequence encoding a first polypeptide of at least 30 amino acids that has at least 70% identity based on the Clustal method of alignment when compared to a polypeptide selected from the group consisting of SEQ ID NOs:2, 4, 6, 8, 10, 12 and 14.

It is preferred that the isolated polynucleotides of the claimed invention consists of a nucleic acid sequence selected from the group consisting of SEQ ID NOs: 1, 3, 5, 7, 9, 11, 13, 15, 17, 19, 21, 23, 25 and 27 that codes for the polypeptide selected from the group consisting of SEQ ID NOs:2, 4, 6, 8, 10, 12, 14, 16, 18, 20, 22, 24, 26 and 28. The present invention also relates to an isolated polynucleotide comprising a nucleotide sequences of at least one of 40 (preferably at least one of 30) contiguous nucleotides derived from a nucleotide sequence selected from the group consisting of SEQ ID NOs:1, 3, 5, 7, 9, 11, 13, 15, 17, 19, 21, 23, 25 and 27 and the complement of such nucleotide sequences.

The present invention relates to a chimeric gene comprising an isolated polynucleotide of the present invention operably linked to suitable regulatory sequences.

The present invention also relates to the identification of transit peptides associated with aminoacyl-tRNA synthetases of the instant invention and the use of those transit peptides to target aminoacyl-tRNA synthetases and other operably linked proteins to specific organelles within plant cells. Transit peptide amino acid sequences are located just upstream of the mature aminoacyl-tRNA synthetase polypeptide sequences disclosed in the instant invention.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a seryl-tRNA synthetase polypeptide of at least 116 amino acids comprising at least 85% homology based on the Clustal method of alignment compared to a polypeptide selected from the group consisting of SEQ ID NOs: 16, 18 and 20.

The present invention also relates to a threonyl-tRNA synthetase polypeptide of at least 483 amino acids comprising at least 80% homology based on the Clustal method of alignment compared to a polypeptide selected from the group consisting of SEQ ID NOs:20, 22, 24, 26 and 28.

The present invention relates to a method of selecting an isolated polynucleotide that affects the level of expression of a seryl-tRNA synthetase or threonyl-tRNA synthetase polypeptide in a host cell, preferably a plant cell, the method comprising the steps of:

constructing an isolated polynucleotide of the present invention or an isolated chimeric gene of the present invention;

introducing the isolated polynucleotide or the isolated chimeric gene into a host cell;

measuring the level a seryl-tRNA synthetase or threonyl-tRNA synthetase polypeptide in the host cell containing the isolated polynucleotide; and comparing the level of a seryl-tRNA synthetase or threonyl-tRNA synthetase polypeptide in the host cell containing the isolated polynucleotide with the level of a seryl-tRNA synthetase or threonyl-tRNA synthetase polypeptide in a host cell that does not contain the isolated polynucleotide.

The present invention relates to a method of obtaining a nucleic acid fragment encoding a substantial portion of a seryl-tRNA synthetase or threonyl-tRNA synthetase polypeptide gene, preferably a plant seryl-tRNA synthetase or threonyl-tRNA synthetase polypeptide gene, comprising the steps of: synthesizing an oligonucleotide primer comprising a nucleotide sequence of at least one of 40 (preferably at least one of 30) contiguous nucleotides derived from a nucleotide sequence selected from the group consisting of SEQ ID NOs:1, 3, 5, 7, 9, 11, 13, 15, 17, 19, 21, 23, 25 and 27 and the complement of such nucleotide sequences; and amplifying a nucleic acid fragment (preferably a cDNA inserted in a cloning vector) using the oligonucleotide primer. The amplified nucleic acid fragment preferably will encode a portion of a seryl-tRNA synthetase or threonyl-tRNA synthetase amino acid sequence.

The present invention also relates to a method of obtaining a nucleic acid fragment encoding all or a substantial portion of the amino acid sequence encoding a seryl-tRNA synthetase or threonyl-tRNA synthetase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a seryl-tRNA synthetase or threonyl-tRNA synthetase, the method comprising the steps of: (a) transforming a host cell with a chimeric gene comprising a nucleic acid fragment encoding an aminoacyl-tRNA synthetase polypeptide, operably linked to suitable regulatory sequences; (b) growing the transformed host cell under conditions that are suitable for expression of the chimeric gene wherein expression of the chimeric gene results in production of an aminoacyl-tRNA synthetase polypeptide in the transformed host cell; (c) optionally purifying the aminoacyl-tRNA synthetase expressed by the transformed host cell; (d) treating the amino-acyl-tRNA synthetase with a compound to be tested; and (e) comparing the activity of the aminoacyl-tRNA synthetase that has been treated with a test compound to the activity of an untreated aminoacyl-tRNA synthetase, thereby selecting compounds with potential for inhibitory activity.

The present invention relates to a composition comprising an isolated polynucleotide or polypeptide of the present invention.

The present invention relates to an expression cassette comprising an isolated polynucleotide of the present invention.

The present invention relates to a method for positive selection of a transformed cell comprising:

(a) transforming a plant cell, preferably a monocot such as corn, with a chimeric gene of the present invention or an expression cassette of the present invention; and (b) growing the transformed plant under conditions allowing expression of the polynucleotide in an amount sufficient to complement an amiono acyl-tRNA synthetase.

As used herein, the following terms shall apply:

"Aminoacyl-tRNA synthetase" refers to seryl-tRNA synthetase and/or threonyl-tRNA synthetase.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"). Nucleotide sequences, SEQ ID NOs:15, 17, 19, 21, 23, 25 and 27 and amino acid sequences SEQ ID NOs:16, 18, 20, 22, 24, 26 and 28 were determined by further sequence analysis of cDNA clones encoding the amino acid sequences set forth in SEQ ID NOs:2, 4, 6, 8, 10, 12 and 14. Nucleotide SEQ ID NOs:1, 3, 5, 7, 9, 11 and 13 and amino acid SEQ ID NOs:2, 4, 6, 8, 10, 12 and 14 were presented in a U.S. Provisional Application No. 60/107,276, filed Nov. 5, 1998.

The sequence descriptions and Sequence Listing attached hereto comply with the rules governing nucleotide and/or amino acid sequence disclosures in patent applications as set forth in 37 C.F.R. §1.821–1.825.

at least one of 60 contiguous nucleotides, preferably at least one of 40 contiguous nucleotides, most preferably one of at least 30 contiguous nucleotides, of the nucleic acid sequence of the SEQ ID NOs:1, 3, 5, 7, 9, 11, 13, 15, 17, 19, 21, 23, 25 and 27.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

TABLE 1

Aminoacyl-tRNA Synthetases

| Protein | Clone Designation | SEQ ID NO: (Nucleotide) | SEQ ID NO: (Amino Acid) |
| --- | --- | --- | --- |
| Seryl-tRNA Synthetase | r1r6.pk0023.e9 (EST) | 1 | 2 |
| Seryl-tRNA Synthetase | s12.pk123.g22 (EST) | 3 | 4 |
| Seryl-tRNA Synthetase | w1m4.pk0018.d5 (EST) | 5 | 6 |
| Threonyl-tRNA Synthetase | cr1n.pk0140.b10 (EST) | 7 | 8 |
| Threonyl-tRNA Synthetase | r1r6.pk0084.e1 (EST) | 9 | 10 |
| Threonyl-tRNA Synthetase | srr1c.pk003.k12 (EST) | 11 | 12 |
| Threonyl-tRNA Synthetase | wr1.pk181.e1 (EST) | 13 | 14 |
| Seryl-tRNA Synthetase | r1r6.pk0023.e9 (CGS) | 15 | 16 |
| Seryl-tRNA Synthetase | s12.pk123.g22 (FIS) | 17 | 18 |
| Seryl-tRNA Synthetase | w1m4.pk0018.d5 (CGS) | 19 | 20 |
| Threonyl-tRNA Synthetase | p0017.cespf50r (CGS) | 21 | 22 |
| Threonyl-tRNA Synthetase | res1c.pk005.j13 (FIS) | 23 | 24 |
| Threonyl-tRNA Synthetase | srr1c.pk003.k12 (FIS) | 25 | 26 |
| Threonyl-tRNA Synthetase | w1m96.pk060.l13 (FIS) | 27 | 28 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25 and 27 and the complement of such nucleotide sequences may be used in methods of selecting an isolated polynucleotide that affects the expression of a polypeptide (such as aminoacyl-tRNA synthetase) in a plant cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) J. Mol. Biol. 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several aminoacyl-tRNA synthetases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other seryl-tRNA synthetase or threonyl-tRNA synthetase polypeptides, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, 23, 25 and 27 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as seryl-tRNA synthetase or threonyl-tRNA synthetase polypeptide) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 23, 25 and 27 and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide (such as aminoacyl-tRNA synthetase polypeptide).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of aminoacyl-tRNA synthetase in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded aminoacyl-tRNA synthetase. An example of a vector for high level expression of the instant polypeptides in a bacterial host is provided (Example 7).

Additionally, the instant polypeptides can be used as a targets to facilitate design and/or identification of inhibitors of those enzymes that may be useful as herbicides. This is desirable because the polypeptides described herein catalyze various steps in aminoacyl-tRNA biosynthesis. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis*: A Practical Guide, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
| --- | --- | --- |
| cr1n | Corn Root From 7 Day Old Seedlings* | cr1n.pk0140.b10 |
| p0017 | Corn Ear Shoot, Prophase I (2.8–4.8 cm) | p0017.cespf50r |
| res1c | Rice Etiolated Seedling | res1c.pk005.j13 |
| r1r6 | Rice Leaf 15 Days After Germination, 6 Hours After Infection of *Magoporthe grisea* Strain 4360-R-62 (AVR2-YAMO); Resistant | r1r6.pk0084.e1 |
| | | r1r6.pk0023.e9 |
| s12 | Soybean Two-Week-Old Developing Seedlings Treated With 2.5 ppm chlorimuron | s12.pk123.g22 |
| srr1c | Soybean 8-Day-Old Root | srr1c.pk003.k12 |
| w1m4 | Wheat Seedlings 4 Hours After Inoculation With *Erysiphe graminis* f. sp *tritici* | w1m4.pk0018.d5 |
| w1m96 | Wheat Seedlings 95 Hours After Inoculation With *Erysiphe graminis* f. sp *tritici* | w1m96.pk060.l13 |
| wr1 | Wheat Root From 7 Day Old Seedling | wr1.pk181.e1 |

*This library was normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2
Identification of cDNA Clones cDNA clones encoding lignin biosynthetic enzymes were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained. in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3
Characterization of cDNA Clones Encoding Seryl-tRNA Synthetase

The BLASTX search using the EST sequences from clones listed in Table 3 revealed similarity of the polypeptides encoded by the cDNAs to seryl-tRNA synthetase from *Zea mays* (NCBI Identifier No. gi 3319776) and *Arabidopsis thaliana* (NCBI Identifier No. gi 2501056). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding Polypeptides Homologous to *Zea mays* and *Arabidopsis thaliana* Seryl-tRNA Synthetase

| Clone | Status | BLAST pLog Score |
| --- | --- | --- |
| r1r6.pk0023.e9 | CGS | >254.00 (gi 3319776) |
| s12.pk123.g22 | FIS | 51.00 (gi 2501056) |
| w1m4.pk0018.d5 | CGS | >254.00 (gi 3319776) |

The data in Table 4 represents a calculation of the percent identity of the amino acid sequences set forth in SEQ ID NOs:16, 18 and 20 and the *Zea mays* and *Arabidopsis thaliana* sequences.

TABLE 4

Percent Identity of Amino Acid Sequences Deduced From the Nucleotide Sequences of cDNA Clones Encoding Polypeptides Homologous to *Zea mays* and *Arabidopsis thaliana* Seryl-tRNA Synthetase

| SEQ ID NO. | Percent Identity to |
| --- | --- |
| 16 | 75% (gi 3319776) |
| 18 | 80% (gi 2501056) |
| 20 | 80% (gi 3319776) |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a seryl-tRNA synthetase. These sequences represent the first rice, soybean and wheat sequences encoding seryl-tRNA synthetase.

Example 4
Characterization of cDNA Clones Encoding Threonyl-tRNA Synthetase The BLASTX search using the EST sequences from clones listed in Table 5 revealed similarity of the polypeptides encoded by the cDNAs to threonyl-tRNA synthetase from *Arabidopsis thaliana* (NCBI Identifier No. gi 3617770). Shown in Table 5 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 5

BLAST Results for Sequences Encoding Polypeptides Homologous to *Arabidopsis thaliana* Threonyl-tRNA Synthetase

| Clone | Status | BLAST pLog Score to gi 3617770 |
| --- | --- | --- |
| p0017.cespf50r | FIS | >254.00 |
| res1c.pk005.j13 | FIS | >254.00 |
| srr1c.pk003.k12 | FIS | >254.00 |
| w1m96.pk060.113 | FIS | >254.00 |

The data in Table 6 represents a calculation of the percent identity of the amino acid sequences set forth in SEQ ID NOs:22, 24, 26 and 28 and the *Arabidopsis thaliana* sequence.

TABLE 6

Percent Identity of Amino Acid Sequences Deduced From the Nucleotide Sequences of cDNA Clones Encoding Polypeptides Homologous to *Arabidopsis thaliana* Threonyl-tRNA Synthetase

| SEQ ID NO. | Percent Identity to |
| --- | --- |
| 22 | 66% |
| 24 | 73% |
| 26 | 76% |
| 28 | 76% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a threonyl-tRNA synthetase. These sequences represent the first corn, rice, soybean and wheatsequences encoding threonyl-tRNA synthetase.

Example 5
Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6
Expression of Chimeric Genes in Dicot Cells

A seed-specific expression cassette composed of the promoter and transcription terminator from the gene encoding the P subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7
Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 8
Evaluating Compounds for Their Ability to Inhibit the Activity of Aminoacyl-tRNA Synthetases The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for aminoacyl-tRNA synthetase activity are presented by (Lloyd et al., (1995) Nucleic Acid Research 23(15):2882–2892).

What is claimed is:

1. An isolated polynucleotide comprising:
   (a) a nucleotide sequence encoding a polypeptide having threonyl-tRNA synthetase activity, wherein the amino acid sequence of the polypeptide and the amino acid sequence of SEQ ID NO:22 have at least 80% sequence identity based on the Clustal alignment method, or
   (b) the complement of the nucleotide sequence, wherein the complement and the nucleotide sequence contain the same number of nucleotides and are 100% complementary was inserted.

2. The polynucleotide of claim 1, wherein the amino acid sequence of the polypeptide and the amino acid sequence of SEQ ID NO:22 have at least 85% sequence identity based on the Clustal alignment method.

3. The polynucleotide of claim 1, wherein the amino acid sequence of the polypeptide and the amino acid sequence of SEQ ID NO:22 have at least 90% sequence identity based on the Clustal alignment method.

4. The polynucleotide of claim 1, wherein the amino acid sequence of the polypeptide and the amino acid sequence of SEQ ID NO:22 have at least 95% sequence identity based on the Clustal alignment method.

5. The polynucleotide of claim 1, wherein the polypeptide comprises the amino acid sequence of SEQ ID NO:22.

6. The polynucleotide of claim 1, wherein the nucleotide sequence comprises the nucleotide sequence of SEQ ID NO:21.

7. A vector comprising the polynucleotide of claim 1.

8. A recombinant DNA construct comprising the polynucleotide of claim 1 operably linked to a regulatory sequence.

9. A method for transforming a cell comprising transforming a cell with the polynucleotide of claim 1.

10. A cell comprising the recombinant DNA construct of claim 8.

11. A method for producing a plant comprising transforming a plant cell with the polynucleotide of claim 1 and regenerating a plant from the transformed plant cell.

12. A plant comprising the recombinant DNA construct of claim 8.

13. A seed comprising the recombinant DNA construct of claim 8.

14. The plant of claim 12, wherein the plant is a corn plant.

* * * * *

UNITED STATES PATENT AND TRADEMARK OFFICE
CERTIFICATE OF CORRECTION

PATENT NO. : 6,696,619 B1
DATED : February 24, 2004
INVENTOR(S) : Famodu, Omolayo O. and Simmons, Carl R.

It is certified that error appears in the above-identified patent and that said Letters Patent is hereby corrected as shown below:

Column 69,
Line 39, after "complementary:" delete "was inserted".

Signed and Sealed this

Twelfth Day of April, 2005

JON W. DUDAS
*Director of the United States Patent and Trademark Office*

SEQUENCE LISTING

<160> NUMBER OF SEQ ID NOS: 28

<210> SEQ ID NO 1
<211> LENGTH: 562
<212> TYPE: DNA
<213> ORGANISM: Oryza sp.
<220> FEATURE:
<221> NAME/KEY: unsure
<222> LOCATION: (431)
<223> OTHER INFORMATION: n = a, c, g or t
<220> FEATURE:
<221> NAME/KEY: unsure
<222> LOCATION: (481)
<223> OTHER INFORMATION: n = a, c, g or t
<220> FEATURE:
<221> NAME/KEY: unsure
<222> LOCATION: (492)
<223> OTHER INFORMATION: n = a, c, g or t
<220> FEATURE:
<221> NAME/KEY: unsure
<222> LOCATION: (498)
<223> OTHER INFORMATION: n = a, c, g or t
<220> FEATURE:
<221> NAME/KEY: unsure
<222> LOCATION: (516)
<223> OTHER INFORMATION: n = a, c, g or t
<220> FEATURE:
<221> NAME/KEY: unsure
<222> LOCATION: (519)
<223> OTHER INFORMATION: n = a, c, g or t
<220> FEATURE:
<221> NAME/KEY: unsure
<222> LOCATION: (521)
<223> OTHER INFORMATION: n = a, c, g or t
<220> FEATURE:
<221> NAME/KEY: unsure
<222> LOCATION: (528)
<223> OTHER INFORMATION: n = a, c, g or t
<220> FEATURE:
<221> NAME/KEY: unsure
<222> LOCATION: (534)
<223> OTHER INFORMATION: n = a, c, g or t
<220> FEATURE:
<221> NAME/KEY: unsure
<222> LOCATION: (548)
<223> OTHER INFORMATION: n = a, c, g or t
<220> FEATURE:
<221> NAME/KEY: unsure
<222> LOCATION: (549)
<223> OTHER INFORMATION: n = a, c, g or t

<400> SEQUENCE: 1

| | | | | | | |
|---|---|---|---|---|---|---|
| gtttaaactc | tacccttccc | tctctgctcg | ccgccgccgc | cgccgccgca | cgccttcgaa | 60 |
| gatgctcgac | atcaacctct | tccgcacgga | gaagggcggc | gacccggagc | tgatccgcag | 120 |
| gtcgcagcgc | aaccgctccg | cctccgtcga | gctcgtcgac | gaggtcatcg | ccctcgacga | 180 |
| ccagtggcgc | cagaggcaat | tcgagctcga | caaaatccgg | caggagctca | acaaaaccag | 240 |
| caaggaaatc | ggcaagctca | aggctaaaaa | ggaggacgcg | tcggctctga | ttcagagcac | 300 |
| ggaagagatt | aagaagaggt | tggctgccaa | ggagacggag | gtgcaggaag | ccaagggcac | 360 |
| gctcgatgcc | aagctcgtga | cgattggaaa | cattgtgcat | gaatccgtcc | ctgtcagcga | 420 |
| tgacgaggct | ncaatttaat | tgtacggaca | tggggaagag | aggctggagg | aatttgaaga | 480 |
| nacgtggatt | tngaaatntt | acatagagct | tgagangtnt | ntgatcangt | gaanggtaca | 540 |
| ttaatganna | gggccactga | ct | | | | 562 |

<210> SEQ ID NO 2
<211> LENGTH: 125

-continued

```
<212> TYPE: PRT
<213> ORGANISM: Oryza sp.
<220> FEATURE:
<221> NAME/KEY: UNSURE
<222> LOCATION: (124)
<223> OTHER INFORMATION: Xaa = any amino acid

<400> SEQUENCE: 2
```

Met Leu Asp Ile Asn Leu Phe Arg Thr Glu Lys Gly Gly Asp Pro Glu
  1               5                  10                  15

Leu Ile Arg Arg Ser Gln Arg Asn Arg Ser Ala Ser Val Glu Leu Val
             20                  25                  30

Asp Glu Val Ile Ala Leu Asp Asp Gln Trp Arg Gln Arg Gln Phe Glu
         35                  40                  45

Leu Asp Lys Ile Arg Gln Glu Leu Asn Lys Thr Ser Lys Glu Ile Gly
     50                  55                  60

Lys Leu Lys Ala Lys Lys Glu Asp Ala Ser Ala Leu Ile Gln Ser Thr
 65                  70                  75                  80

Glu Glu Ile Lys Lys Arg Leu Ala Ala Lys Glu Thr Glu Val Gln Glu
                 85                  90                  95

Ala Lys Gly Thr Leu Asp Ala Lys Leu Val Thr Ile Gly Asn Ile Val
            100                 105                 110

His Glu Ser Val Pro Val Ser Asp Asp Glu Ala Xaa Ile
            115                 120                 125

```
<210> SEQ ID NO 3
<211> LENGTH: 489
<212> TYPE: DNA
<213> ORGANISM: Glycine max

<400> SEQUENCE: 3
```
atgatgctgc agcaaagaag tatgatctag aagcatggtt tccagcctct caagcttaca      60
gagagctagt gtcctgttca aactgtacag actatcaggc cagaagatta gaaattcgat     120
atggtcagaa aaagagcaat gagcaaatga agcaatatgt tcacttgttg aactctactc     180
taacggctac tgagaggacc atttgctgca tactagagaa caaccagaag gaagatgggg     240
tagagatacc agaagccctc aggccattca tgggtggaaa gactttccta cctttcaaga     300
accaaccatc taatgaagcc aaagggaaga atcgaaggc ctaattgcat tttaagtcag     360
tgatatttat gaagagtttg ttcagagttg taggttatga tgaccccgat attatccacc     420
acacactgtt tcccttctc actaaatagt aaaatgattt ttaggagcac gcaccatttt     480
tgggtcaaa                                                             489

```
<210> SEQ ID NO 4
<211> LENGTH: 102
<212> TYPE: PRT
<213> ORGANISM: Glycine max

<400> SEQUENCE: 4
```

Asp Ala Ala Ala Lys Lys Tyr Asp Leu Glu Ala Trp Phe Pro Ala Ser
  1               5                  10                  15

Gln Ala Tyr Arg Glu Leu Val Ser Cys Ser Asn Cys Thr Asp Tyr Gln
             20                  25                  30

Ala Arg Arg Leu Glu Ile Arg Tyr Gly Gln Lys Lys Ser Asn Glu Gln
         35                  40                  45

Met Lys Gln Tyr Val His Leu Leu Asn Ser Thr Leu Thr Ala Thr Glu
     50                  55                  60

```
Arg Thr Ile Cys Cys Ile Leu Glu Asn Asn Gln Lys Glu Asp Gly Val
 65                  70                  75                  80

Glu Ile Pro Glu Ala Leu Arg Pro Phe Met Gly Gly Lys Thr Phe Leu
                 85                  90                  95

Pro Phe Lys Asn Gln Pro
            100

<210> SEQ ID NO 5
<211> LENGTH: 641
<212> TYPE: DNA
<213> ORGANISM: Triticum sp.
<220> FEATURE:
<221> NAME/KEY: unsure
<222> LOCATION: (354)
<223> OTHER INFORMATION: n = a, c, g or t
<220> FEATURE:
<221> NAME/KEY: unsure
<222> LOCATION: (424)
<223> OTHER INFORMATION: n = a, c, g or t
<220> FEATURE:
<221> NAME/KEY: unsure
<222> LOCATION: (482)
<223> OTHER INFORMATION: n = a, c, g or t
<220> FEATURE:
<221> NAME/KEY: unsure
<222> LOCATION: (511)
<223> OTHER INFORMATION: n = a, c, g or t
<220> FEATURE:
<221> NAME/KEY: unsure
<222> LOCATION: (524)
<223> OTHER INFORMATION: n = a, c, g or t
<220> FEATURE:
<221> NAME/KEY: unsure
<222> LOCATION: (528)
<223> OTHER INFORMATION: n = a, c, g or t
<220> FEATURE:
<221> NAME/KEY: unsure
<222> LOCATION: (540)
<223> OTHER INFORMATION: n = a, c, g or t
<220> FEATURE:
<221> NAME/KEY: unsure
<222> LOCATION: (553)
<223> OTHER INFORMATION: n = a, c, g or t
<220> FEATURE:
<221> NAME/KEY: unsure
<222> LOCATION: (556)
<223> OTHER INFORMATION: n = a, c, g or t
<220> FEATURE:
<221> NAME/KEY: unsure
<222> LOCATION: (557)
<223> OTHER INFORMATION: n = a, c, g or t
<220> FEATURE:
<221> NAME/KEY: unsure
<222> LOCATION: (566)
<223> OTHER INFORMATION: n = a, c, g or t
<220> FEATURE:
<221> NAME/KEY: unsure
<222> LOCATION: (568)
<223> OTHER INFORMATION: n = a, c, g or t
<220> FEATURE:
<221> NAME/KEY: unsure
<222> LOCATION: (572)
<223> OTHER INFORMATION: n = a, c, g or t
<220> FEATURE:
<221> NAME/KEY: unsure
<222> LOCATION: (582)
<223> OTHER INFORMATION: n = a, c, g or t
<220> FEATURE:
<221> NAME/KEY: unsure
<222> LOCATION: (600)..(601)
<223> OTHER INFORMATION: n = a, c, g or t
<220> FEATURE:
<221> NAME/KEY: unsure
<222> LOCATION: (611)
<223> OTHER INFORMATION: n = a, c, g or t
<220> FEATURE:
```

```
<221> NAME/KEY: unsure
<222> LOCATION: (618)
<223> OTHER INFORMATION: n = a, c, g or t
<220> FEATURE:
<221> NAME/KEY: unsure
<222> LOCATION: (623)
<223> OTHER INFORMATION: n = a, c, g or t
<220> FEATURE:
<221> NAME/KEY: unsure
<222> LOCATION: (641)
<223> OTHER INFORMATION: n = a, c, g or t

<400> SEQUENCE: 5
ccgtcatcca cctctcgtca gaagaacccct ccctctccgc cctccgccgc cgccgccgcc    60
gccgccaatc gcagcgcagc cgcctcgccc ccgtcgagct cgtccgcgga gaagttggcc   120
tagccgcggt cgcacgagaa tatgctcgac atcaacctct tccgcaagga gaagggcggc   180
gaccctgagc tcgtccgcca gtcgcagcgc agccgcttcg ccccgtcga gctcgtcgac    240 gaggtcatcg tcctcgacga ggcgtggcgc cagaggcagt tcgagctcga caagatccgg   300
caggagctca acaaaaccag caaggagatc ggcaagctca aggccaaaaa gcangatgcg   360
acggagctga tacagagcac ggagggagat taagaagagg ctggccgcca aggagacgga   420
cgtncaggag gcaagacacc tcgatgcaag ctagttacat cggcaactcg tgcatgatct   480
gnccataaca acgacgagca acatctttg ncggcatggg caanaaaanat ggggagaatn   540 aagatcagtg gtnctnnaaa tgctgnanct ancttgaaag gnctagttct gggaaaggtn   600
ntttaaggga nggttccnaa cangttaaaa tttggcatat n                       641

<210> SEQ ID NO 6
<211> LENGTH: 81
<212> TYPE: PRT
<213> ORGANISM: Triticum sp.
<220> FEATURE:
<221> NAME/KEY: UNSURE
<222> LOCATION: (71)
<223> OTHER INFORMATION: Xaa = any amino acid

<400> SEQUENCE: 6

Met Leu Asp Ile Asn Leu Phe Arg Lys Glu Lys Gly Gly Asp Pro Glu
  1               5                  10                  15

Leu Val Arg Gln Ser Gln Arg Ser Arg Phe Ala Pro Val Glu Leu Val
             20                  25                  30

Asp Glu Val Ile Val Leu Asp Glu Ala Trp Arg Gln Arg Gln Phe Glu
         35                  40                  45

Leu Asp Lys Ile Arg Gln Glu Leu Asn Lys Thr Ser Lys Glu Ile Gly
     50                  55                  60

Lys Leu Lys Ala Lys Lys Xaa Asp Ala Thr Glu Leu Ile Gln Ser Thr
 65                  70                  75                  80

Glu

<210> SEQ ID NO 7
<211> LENGTH: 536
<212> TYPE: DNA
<213> ORGANISM: Zea mays
<220> FEATURE:
<221> NAME/KEY: unsure
<222> LOCATION: (333)
<223> OTHER INFORMATION: n = a, c, g or t
<220> FEATURE:
<221> NAME/KEY: unsure
<222> LOCATION: (377)
<223> OTHER INFORMATION: n = a, c, g or t
<220> FEATURE:
```

<220> FEATURE:
<221> NAME/KEY: unsure
<222> LOCATION: (428)
<223> OTHER INFORMATION: n = a, c, g or t
<220> FEATURE:
<221> NAME/KEY: unsure
<222> LOCATION: (445)
<223> OTHER INFORMATION: n = a, c, g or t
<220> FEATURE:
<221> NAME/KEY: unsure
<222> LOCATION: (448)
<223> OTHER INFORMATION: n = a, c, g or t
<220> FEATURE:
<221> NAME/KEY: unsure
<222> LOCATION: (493)
<223> OTHER INFORMATION: n = a, c, g or t
<220> FEATURE:
<221> NAME/KEY: unsure
<222> LOCATION: (498)
<223> OTHER INFORMATION: n = a, c, g or t
<220> FEATURE:
<221> NAME/KEY: unsure
<222> LOCATION: (523)
<223> OTHER INFORMATION: n = a, c, g or t
<220> FEATURE:
<221> NAME/KEY: unsure
<222> LOCATION: (531)
<223> OTHER INFORMATION: n = a, c, g or t

<400> SEQUENCE: 7

```
gaaacttgga acaaagctga gcaacaattg acagaagctt taaatgagtt tgggaagcca      60
tggaagatta atgaaggga tggtgctttc tacggcccaa aaattgatat tggtgtgttt     120
gatgcccttt agaggaaatt tcagtgtgca accctacagc tggattttca gctgcccatt    180
cggttcaagc tggcttattc tgctgaggat gaagccaaaa ttgaaaggcc tgtgatgata    240
cacagggcaa tcctaggttc ggttgaaagg atgcttgcca ttcttttggg agcattacaa    300
tggtaaatgg ccttatggct aaccctcgcc agncattgtt tgctcggtac ttctggtcag    360
tggatatgcc aaacaantcc tgccactcca catgaactgg tttcatgttg atattgaccc    420
aatgacanga caatacaaaa gaagnacngg aactcaactg gccaatcaac tacatcctgt    480
cgtagtgcac aanaagcnag acgggaatat atccttaggg aanagaaatc nactgt       536
```

<210> SEQ ID NO 8
<211> LENGTH: 95
<212> TYPE: PRT
<213> ORGANISM: Zea mays

<400> SEQUENCE: 8

```
Glu Thr Trp Asn Lys Ala Glu Gln Gln Leu Thr Glu Ala Leu Asn Glu
  1               5                  10                  15
Phe Gly Lys Pro Trp Lys Ile Asn Glu Gly Asp Gly Ala Phe Tyr Gly
                 20                  25                  30
Pro Lys Ile Asp Ile Gly Val Phe Asp Ala Leu Lys Arg Lys Phe Gln
             35                  40                  45
Cys Ala Thr Leu Gln Leu Asp Phe Gln Leu Pro Ile Arg Phe Lys Leu
     50                  55                  60
Ala Tyr Ser Ala Glu Asp Glu Ala Lys Ile Glu Arg Pro Val Met Ile
 65                  70                  75                  80
His Arg Ala Ile Leu Gly Ser Val Glu Arg Met Leu Ala Ile Leu
                 85                  90                  95
```

<210> SEQ ID NO 9
<211> LENGTH: 425
<212> TYPE: DNA
<213> ORGANISM: Oryza sp.

```
<220> FEATURE:
<221> NAME/KEY: unsure
<222> LOCATION: (249)
<223> OTHER INFORMATION: n = a, c, g or t
<220> FEATURE:
<221> NAME/KEY: unsure
<222> LOCATION: (283)
<223> OTHER INFORMATION: n = a, c, g or t
<220> FEATURE:
<221> NAME/KEY: unsure
<222> LOCATION: (286)
<223> OTHER INFORMATION: n = a, c, g or t

<400> SEQUENCE: 9
gtttaaacga ttcatagagc tatccttggg tctttggaac gattttttgg tgtcctcatt      60
gaacactatg ctggtgattt ccactttgg cttgcaccaa tccaagctcg tattctacct     120
gtgacagaca atgagctgca atactgtaac gaggtggctt cagaactgaa atcaaaaggc    180
attccgagct gaggtatgtc atggcgagcg tctaccaaag ctaatacgga atgcccgaaa    240
cgaagaaant gccgctcatg gcggccttg gggcctaaag aantcnaagc aaggaccctc    300
cactacaggc caagcatagt ggggaattgg gactatgcct gtgggatgat ccttcgcag    360 aaccaacttg ctattggcga caacctcct caactaatga catttaaat atgctaaaga    420 cagtt                                                                425

<210> SEQ ID NO 10
<211> LENGTH: 58
<212> TYPE: PRT
<213> ORGANISM: Oryza sp.

<400> SEQUENCE: 10

Ile His Arg Ala Ile Leu Gly Ser Leu Glu Arg Phe Phe Gly Val Leu
  1               5                  10                  15

Ile Glu His Tyr Ala Gly Asp Phe Pro Leu Trp Leu Ala Pro Ile Gln
             20                  25                  30

Ala Arg Ile Leu Pro Val Thr Asp Asn Glu Leu Gln Tyr Cys Asn Glu
         35                  40                  45

Val Ala Ser Glu Leu Lys Ser Lys Gly Ile
     50                  55

<210> SEQ ID NO 11
<211> LENGTH: 508
<212> TYPE: DNA
<213> ORGANISM: Glycine max
<220> FEATURE:
<221> NAME/KEY: unsure
<222> LOCATION: (467)
<223> OTHER INFORMATION: n = a, c, g or t

<400> SEQUENCE: 11
acactatgct atgctatgct ctctaatccg tttccgccgt tacgctcctt cctaccgcac      60
tctccactct ctctttccga cgattaaccg tttctcctcc tccgtctcct ccgcctccgc    120
cgccatggtt gctcacgcga aggacgaggc gtacctcagc gcgacgattc cgaaacgcat    180
ccgtctcttc gagaccatcc tggcggagca gcacactcag cgcctctcgc tctccccgga    240
tcctatcaag gttactctcc ccgacggcag cgtcaaggag gcgaagaagt ggcatacgac    300
gccgcttgat gttgcgcgtg aaatctcgaa gaatttggcc aacagcgcgc tcatcgcgaa    360
ggtcaatggc gtgctctggg acatgactcg ccctctcgag gacgattgcc aagctccaga    420
tcttcaagtt cgacgacgac gaaggccgcg acaccttctg ggactcnagc gcccacattc    480
```

```
tcgggcaagt cacttgagac ggatatgg                                        508
```

<210> SEQ ID NO 12
<211> LENGTH: 80
<212> TYPE: PRT
<213> ORGANISM: Glycine max

<400> SEQUENCE: 12

```
Ile Pro Lys Arg Ile Arg Leu Phe Glu Thr Ile Leu Ala Glu Gln His
 1               5                  10                  15

Thr Gln Arg Leu Ser Leu Ser Pro Asp Pro Ile Lys Val Thr Leu Pro
            20                  25                  30

Asp Gly Ser Val Lys Glu Ala Lys Lys Trp His Thr Thr Pro Leu Asp
        35                  40                  45

Val Ala Arg Glu Ile Ser Lys Asn Leu Ala Asn Ser Ala Leu Ile Ala
    50                  55                  60

Lys Val Asn Gly Val Leu Trp Asp Met Thr Arg Pro Leu Glu Asp Asp
65                  70                  75                  80
```

<210> SEQ ID NO 13
<211> LENGTH: 487
<212> TYPE: DNA
<213> ORGANISM: Triticum sp.
<220> FEATURE:
<221> NAME/KEY: unsure
<222> LOCATION: (467)
<223> OTHER INFORMATION: n = a, c, g or t

<400> SEQUENCE: 13

```
gttattaggg cagtcccaga aactcttctt tttccatcca cttagcccag gtagctgctt     60
cttccttcca aatggcgcta taatatataa caaattgatg gatttttttgc gcaaggagta   120
tagagagaga ggctaccaag aggttctgag tccaaatatt tacaacatgc aactttggga   180
aacctctgga catgctgcaa actacaagga caacatgttt gttttttgaga tcgagaaaca   240
agaatttggc cttaagccaa tgaattgtcc tggccattgc ctaatgtttg acacgaggt    300
tcgatcgtat agagagttgc ctctccgcat ggctgatttt gggagttctg cacagaaatg   360
aacttagtgg gtgcacttac aggttttgaca cgtgtcagaa gatccaacag gacgatgccc   420
atattttttg cacggagagc aaatcaagga tgaagttcgg gcttgcntgg gagtcaatga   480
tatgtta                                                              487
```

<210> SEQ ID NO 14
<211> LENGTH: 146
<212> TYPE: PRT
<213> ORGANISM: Triticum sp.

<400> SEQUENCE: 14

```
Leu Gly Gln Ser Gln Lys Leu Phe Phe His Pro Leu Ser Pro Gly
 1               5                  10                  15

Ser Cys Phe Phe Leu Pro Asn Gly Ala Ile Ile Tyr Asn Lys Leu Met
            20                  25                  30

Asp Phe Leu Arg Lys Glu Tyr Arg Glu Arg Gly Tyr Gln Glu Val Leu
        35                  40                  45

Ser Pro Asn Ile Tyr Asn Met Gln Leu Trp Glu Thr Ser Gly His Ala
    50                  55                  60

Ala Asn Tyr Lys Asp Asn Met Phe Val Phe Glu Ile Glu Lys Gln Glu
65                  70                  75                  80

Phe Gly Leu Lys Pro Met Asn Cys Pro Gly His Cys Leu Met Phe Gly
```

|   | 85 |   |   |   | 90 |   |   |   | 95 |   |   |   |
|---|---|---|---|---|---|---|---|---|---|---|---|---|
| His | Glu | Val | Arg | Ser | Tyr | Arg | Glu | Leu | Pro | Leu | Arg | Met | Ala | Asp | Phe |
|   |   |   | 100 |   |   |   |   | 105 |   |   |   |   | 110 |   |   |

Gly Val Leu His Arg Asn Glu Leu Ser Gly Cys Thr Tyr Arg Phe Asp
        115                 120                 125

Thr Cys Gln Lys Ile Gln Gln Asp Asp Ala His Ile Phe Cys Thr Glu
    130                 135                 140

Ser Lys
145

<210> SEQ ID NO 15
<211> LENGTH: 1753
<212> TYPE: DNA
<213> ORGANISM: Oryza sativa

<400> SEQUENCE: 15

```
gcacgaggtt taaactctac ccttccctct ctgctcgccg ccgccgccgc cgccgcacgc     60
cttcgaagat gctcgacatc aacctcttcc gcacggagaa gggcggcgac ccggagctga    120
tccgcaggtc gcagcgcaac cgctccgcct ccgtcgagct cgtcgacgag gtcatcgccc    180
tcgacgacca gtggcgccag aggcaattcg agctcgacaa atccggcag gagctcaaca     240
aaaccagcaa ggaaatcggc aagctcaagg ctaaaaagga ggacgcgtcg gctctgattc    300
agagcacgga agagattaag aagaggttgg ctgccaagga cggaggtg caggaggcca     360
agggcacgct cgatgccaag ctcgtgacga ttggaaacat tgtgcatgaa tccgtccctg    420
tcagcgatga cgaggctaac aatttaattg tacggacatg gggagagagg aggctggagg    480
gtaatttgaa gaatcacgtg gatctttgta agatgcttga catagtagct ttggagaaag    540
gtgctgatgt agcaggtgga aggggttact atttaaagga tgaaggtgtc ctactgaact    600
tggcattgat aaattttgga ctcgcttttc tgagaaagcg aggcttcaag ccaatgcaaa    660
ctccttttt catgagaaag gaaaccatgg gaaaatgtgc ccagttggcc caatttgacg    720
aagagcttta caagctaaca ggcgatggag aggaaaagta tctcatcgct acatccgagc    780
aaccgctgtg tgcgtatcat ctaggtgatc gaatttatcc tgctgaattg ccaattagat    840
atgctggata ttccacctgc ttccggaaag aagctggttc acatggaagg gacacggctg    900
gtatcttcag agtccaccaa ttcgaaaaga ttgagcaatt ctgtgttaca gtccaaatg     960
acaatgaatc ctgggagatg catgaagaaa tgataaaaaa ttcagaagat ttctacaagg   1020
agattggcct accgtaccaa cttgtctcca ttgtgtctgg tgctcttaat gatgctgcag   1080
ctaagaagta tgatttagaa gcatggttcc ctgcatcaaa aacctatagg gaattagtgt   1140
cctgctcaaa ttgcacagat tttcaagcaa ggagacttgg tataggttat ggccagaaaa   1200
agaatgatag caatccaagc aattcgttca tatgttgaac tcaacattga ctgccactga   1260
gaggacccct tgctgtattt tggagaactt ccagaaggag aatggtgtcg aagttccaaa   1320
agcattgcag cctacatgg gtggaatcga tttccttcct ttcaagctgg atagcaaaca    1380
agttgctcga ctccaaatca ataatccaa attcaaaggg agatgctatc tgagctagat    1440
gaggaatcaa caaagatttt cttgctttca gacactactg gatgttattc atacttctaa   1500
aaaatgcgtt tgttcagaac ttgtatcaat gatcatgatg ttacagtttt ggctctcatt   1560
tgagtgtatt gattagcaca atgtctgacc atgtacttgc acagtgatat tccgtagaat   1620
gtctggctat cttggacatg tgcgcttaat ttgccgtaaa agatgtattc attttcatgg   1680
cctttagtgc ctatactaat ttgttgcata caaaaaaaaa aaaaaaaaaa aaaaaaaaaa   1740
```
aaaaaaaaaa aaa                                                                                     1753

<210> SEQ ID NO 16
<211> LENGTH: 453
<212> TYPE: PRT
<213> ORGANISM: Oryza sativa
<220> FEATURE:
<221> NAME/KEY: UNSURE
<222> LOCATION: (390)
<223> OTHER INFORMATION: Xaa = any amino acid
<220> FEATURE:
<221> NAME/KEY: UNSURE
<222> LOCATION: (394)
<223> OTHER INFORMATION: Xaa = any amino acid

<400> SEQUENCE: 16

```
Met Leu Asp Ile Asn Leu Phe Arg Thr Glu Lys Gly Gly Asp Pro Glu
  1               5                  10                  15

Leu Ile Arg Arg Ser Gln Arg Asn Arg Ser Ala Ser Val Glu Leu Val
             20                  25                  30

Asp Glu Val Ile Ala Leu Asp Asp Gln Trp Arg Gln Arg Gln Phe Glu
         35                  40                  45

Leu Asp Lys Ile Arg Gln Glu Leu Asn Lys Thr Ser Lys Glu Ile Gly
     50                  55                  60

Lys Leu Lys Ala Lys Lys Glu Asp Ala Ser Ala Leu Ile Gln Ser Thr
 65                  70                  75                  80

Glu Glu Ile Lys Lys Arg Leu Ala Ala Lys Glu Thr Glu Val Gln Glu
                 85                  90                  95

Ala Lys Gly Thr Leu Asp Ala Lys Leu Val Thr Ile Gly Asn Ile Val
            100                 105                 110

His Glu Ser Val Pro Val Ser Asp Asp Glu Ala Asn Asn Leu Ile Val
        115                 120                 125

Arg Thr Trp Gly Glu Arg Arg Leu Glu Gly Asn Leu Lys Asn His Val
    130                 135                 140

Asp Leu Cys Lys Met Leu Asp Ile Val Ala Leu Glu Lys Gly Ala Asp
145                 150                 155                 160

Val Ala Gly Gly Arg Gly Tyr Tyr Leu Lys Asp Glu Gly Val Leu Leu
                165                 170                 175

Asn Leu Ala Leu Ile Asn Phe Gly Leu Ala Phe Leu Arg Lys Arg Gly
            180                 185                 190

Phe Lys Pro Met Gln Thr Pro Phe Phe Met Arg Lys Glu Thr Met Gly
        195                 200                 205

Lys Cys Ala Gln Leu Ala Gln Phe Asp Glu Glu Leu Tyr Lys Leu Thr
    210                 215                 220

Gly Asp Gly Glu Glu Lys Tyr Leu Ile Ala Thr Ser Glu Gln Pro Leu
225                 230                 235                 240

Cys Ala Tyr His Leu Gly Asp Arg Ile Tyr Pro Ala Glu Leu Pro Ile
                245                 250                 255

Arg Tyr Ala Gly Tyr Ser Thr Cys Phe Arg Lys Glu Ala Gly Ser His
            260                 265                 270

Gly Arg Asp Thr Ala Gly Ile Phe Arg Val His Gln Phe Glu Lys Ile
        275                 280                 285

Glu Gln Phe Cys Val Thr Ser Pro Asn Asp Asn Glu Ser Trp Glu Met
    290                 295                 300

His Glu Glu Met Ile Lys Asn Ser Glu Asp Phe Tyr Lys Glu Ile Gly
305                 310                 315                 320
```

```
Leu Pro Tyr Gln Leu Val Ser Ile Val Ser Gly Ala Leu Asn Asp Ala
            325                 330                 335

Ala Ala Lys Lys Tyr Asp Leu Glu Ala Trp Phe Pro Ala Ser Lys Thr
        340                 345                 350

Tyr Arg Glu Leu Val Ser Cys Ser Asn Cys Thr Asp Phe Gln Ala Arg
            355                 360                 365

Arg Leu Gly Ile Gly Tyr Gly Lys Lys Asn Asp Ser Asn Pro Ser
    370                 375                 380

Asn Ser Phe Ile Cys Xaa Thr Gln His Xaa Leu Pro Leu Arg Gly Pro
385                 390                 395                 400

Phe Ala Val Phe Trp Arg Thr Ser Arg Arg Met Val Ser Lys Phe
                405                 410                 415

Gln Lys His Cys Ser Leu Thr Trp Val Glu Ser Ile Ser Phe Leu Ser
            420                 425                 430

Ser Trp Ile Ala Asn Lys Leu Leu Asp Ser Lys Ser Asn Asn Pro Asn
        435                 440                 445

Ser Lys Gly Asp Ala
    450
```

<210> SEQ ID NO 17
<211> LENGTH: 554
<212> TYPE: DNA
<213> ORGANISM: Glycine max

<400> SEQUENCE: 17

```
cgcacgagat gatgctgcag caaagaagta tgatctagaa gcatggtttc cagcctctca      60
agcttacaga gagctagtgt cctgttcaaa ctgtacagac tatcaggcca gaagattaga     120
aattcgatat ggtcagaaaa agagcaatga gcaaatgaag caatatgttc acttgttgaa     180
ctctactcta acggctactg agaggaccat ttgctgcata ctagaaaca accagaagga     240
agatggggta gagataccag aagccctcag gccattcatg ggtggaaaga ctttcctacc     300
tttcaagaac caaccatcta atgaagccaa agggaagaaa tcgaaggcct aattgcattt     360
taagtcagtg atatttatga agagtttgtt cagagttgta ggttatgatg accccgatat     420
tatccaccac acactgtttc cctttctcac taaatagtaa aatgattttt aggagcacgc     480
accatttttg gtcaaagtac acagcatgac attttctgta attcattact ctaaaaaatt     540
tgtgcttttt taac                                                      554
```

<210> SEQ ID NO 18
<211> LENGTH: 116
<212> TYPE: PRT
<213> ORGANISM: Glycine max

<400> SEQUENCE: 18

```
Ala Arg Asp Asp Ala Ala Ala Lys Lys Tyr Asp Leu Glu Ala Trp Phe
  1               5                  10                  15

Pro Ala Ser Gln Ala Tyr Arg Glu Leu Val Ser Cys Ser Asn Cys Thr
             20                  25                  30

Asp Tyr Gln Ala Arg Arg Leu Glu Ile Arg Tyr Gly Gln Lys Lys Ser
         35                  40                  45

Asn Glu Gln Met Lys Gln Tyr Val His Leu Leu Asn Ser Thr Leu Thr
     50                  55                  60

Ala Thr Glu Arg Thr Ile Cys Cys Ile Leu Glu Asn Asn Gln Lys Glu
 65                  70                  75                  80

Asp Gly Val Glu Ile Pro Glu Ala Leu Arg Pro Phe Met Gly Gly Lys
```

Thr Phe Leu Pro Phe Lys Asn Gln Pro Ser Asn Glu Ala Lys Gly Lys
         85              90                  95

Lys Ser Lys Ala
    115

<210> SEQ ID NO 19
<211> LENGTH: 1719
<212> TYPE: DNA
<213> ORGANISM: Triticum aestivum

<400> SEQUENCE: 19

| | | | | | |
|---|---|---|---|---|---|
| ccgtcatcca | cctctcgtca | gaagaaccct | ccctctccgc | cctccgccgc | cgccgccgcc | 60 |
| gccgccaatc | gcagcgcagc | cgcctcgccc | ccgtcgagct | cgtccgcgga | gaagttggcc | 120 |
| tagccgcggt | cgcacgagaa | tatgctcgac | atcaacctct | tccgcaagga | gaagggcggc | 180 |
| gaccctgagc | tcgtccgcca | gtcgcagcgc | agccgcttcg | ccccgtcga | gctcgtcgac | 240 |
| gaggtcatcg | tcctcgacga | ggcgtggcgc | cagaggcagt | tcgagctcga | caagatccgg | 300 |
| caggagctca | acaaaaccag | caaggagatc | ggcaagctca | aggccaaaaa | gcaggatgcg | 360 |
| acggagctga | tacagagcac | ggaggagatt | aagaagaggc | tggccgccaa | ggagacggac | 420 |
| gtgcaggagg | ccaagaccac | cctcgatgcc | aagctagtta | ccatcggcaa | cctcgtgcat | 480 |
| gaatctgtgc | ccatcagcaa | cgacgaggca | acaatgcta | ttgtgcggac | atggggcgag | 540 |
| aagagactgg | aggagaaatt | gaagaatcat | gtggatcttt | gcataatgct | tgacatcgta | 600 |
| tctttggata | agggtgctga | tgtagctggt | ggaagaggtt | tcttttttgaa | gggtgacggt | 660 |
| gttctcctga | accaggcgtt | gataaatttt | gggctatcat | tcctgggaaa | acgagaattt | 720 |
| acaccaatgc | aaactccttt | tttcatgaga | aaggagatca | tggcaaaatg | tgcccagttg | 780 |
| gcccaatttg | atgaggagct | ctacaaagta | acaggtgacg | gagaggataa | gtatctcata | 840 |
| gcaacatcgg | agcaaccgct | atgtgcttat | catctaggtg | atcgaatta | tcctgcagat | 900 |
| ttgcctatca | gatatgctgg | gttctccacg | tgcttccgga | agaagctgg | ttcacacggg | 960 |
| agggacacag | ctggcatctt | cagagtccac | cagtttgaaa | agatcgagca | gttctgcgcc | 1020 |
| acaggtccaa | atgacaatgt | atcctgggaa | atgcatgagg | atgattaa | aaatgcagaa | 1080 |
| gattttatc | aggcgattgg | gctaccatat | caactagttt | caattgtctc | tggtgctctt | 1140 |
| aatgatgctg | cagctaagaa | gtatgatttg | gaagcatggt | tccctgcatc | aaaaaccttc | 1200 |
| cgagaattag | tgtcctgttc | aaattgcaca | gattatcagg | caaggagact | tggaataggc | 1260 |
| tatggccaga | aaaagaatga | tgagcaatcg | aagcagttcg | ttcatatgtt | gaattccacg | 1320 |
| ctgactgcaa | ctgagaggac | actttgctgt | attctggaga | actaccagcg | ggaaggtggt | 1380 |
| gttgaagtgc | cagaggtgtt | gcggccattc | atgcttggaa | tagatttcct | tcctttcaag | 1440 |
| cggcctcttg | ttgatagcaa | acaagctgct | gctgactcca | aacccaataa | gtctaaacca | 1500 |
| aagggaaatg | cagcttgaac | tgaaaattgt | ttccaggcag | ataatgatgc | acccttcctt | 1560 |
| ttattaattt | caagaatggt | ctgtagcatg | atgatgattt | ggtctcccat | tttggatggt | 1620 |
| tttggttacg | aagtattgca | atccaggaca | cataatttac | cgcaaagtat | attaatgttt | 1680 |
| ttcatgacta | aaaaaaaaaa | aaaaaaaact | cgagactag | | | 1719 |

<210> SEQ ID NO 20
<211> LENGTH: 458
<212> TYPE: PRT
<213> ORGANISM: Triticum aestivum

<400> SEQUENCE: 20

```
Met Leu Asp Ile Asn Leu Phe Arg Lys Glu Lys Gly Gly Asp Pro Glu
 1               5                  10                  15
Leu Val Arg Gln Ser Gln Arg Ser Arg Phe Ala Pro Val Glu Leu Val
                20                  25                  30
Asp Glu Val Ile Val Leu Asp Glu Ala Trp Arg Gln Arg Gln Phe Glu
            35                  40                  45
Leu Asp Lys Ile Arg Gln Glu Leu Asn Lys Thr Ser Lys Glu Ile Gly
        50                  55                  60
Lys Leu Lys Ala Lys Lys Gln Asp Ala Thr Glu Leu Ile Gln Ser Thr
65                  70                  75                  80
Glu Glu Ile Lys Lys Arg Leu Ala Ala Lys Glu Thr Asp Val Gln Glu
                85                  90                  95
Ala Lys Thr Thr Leu Asp Ala Lys Leu Val Thr Ile Gly Asn Leu Val
            100                 105                 110
His Glu Ser Val Pro Ile Ser Asn Asp Glu Ala Asn Asn Ala Ile Val
        115                 120                 125
Arg Thr Trp Gly Glu Lys Arg Leu Glu Glu Lys Leu Lys Asn His Val
    130                 135                 140
Asp Leu Cys Ile Met Leu Asp Ile Val Ser Leu Asp Lys Gly Ala Asp
145                 150                 155                 160
Val Ala Gly Gly Arg Gly Phe Phe Leu Lys Gly Asp Gly Val Leu Leu
                165                 170                 175
Asn Gln Ala Leu Ile Asn Phe Gly Leu Ser Phe Leu Gly Lys Arg Glu
            180                 185                 190
Phe Thr Pro Met Gln Thr Pro Phe Phe Met Arg Lys Glu Ile Met Ala
        195                 200                 205
Lys Cys Ala Gln Leu Ala Gln Phe Asp Glu Glu Leu Tyr Lys Val Thr
    210                 215                 220
Gly Asp Gly Glu Asp Lys Tyr Leu Ile Ala Thr Ser Glu Gln Pro Leu
225                 230                 235                 240
Cys Ala Tyr His Leu Gly Asp Arg Ile Tyr Pro Ala Asp Leu Pro Ile
                245                 250                 255
Arg Tyr Ala Gly Phe Ser Thr Cys Phe Arg Lys Glu Ala Gly Ser His
            260                 265                 270
Gly Arg Asp Thr Ala Gly Ile Phe Arg Val His Gln Phe Glu Lys Ile
        275                 280                 285
Glu Gln Phe Cys Ala Thr Gly Pro Asn Asp Asn Val Ser Trp Glu Met
    290                 295                 300
His Glu Glu Met Ile Lys Asn Ala Glu Asp Phe Tyr Gln Ala Ile Gly
305                 310                 315                 320
Leu Pro Tyr Gln Leu Val Ser Ile Val Ser Gly Ala Leu Asn Asp Ala
                325                 330                 335
Ala Ala Lys Lys Tyr Asp Leu Glu Ala Trp Phe Pro Ala Ser Lys Thr
            340                 345                 350
Phe Arg Glu Leu Val Ser Cys Ser Asn Cys Thr Asp Tyr Gln Ala Arg
        355                 360                 365
Arg Leu Gly Ile Gly Tyr Gly Lys Lys Asn Asp Glu Gln Ser Lys
    370                 375                 380
Gln Phe Val His Met Leu Asn Ser Thr Leu Thr Ala Thr Glu Arg Thr
385                 390                 395                 400
Leu Cys Cys Ile Leu Glu Asn Tyr Gln Arg Glu Gly Gly Val Glu Val
```

```
                    405                 410                 415
       Pro Glu Val Leu Arg Pro Phe Met Leu Gly Ile Asp Phe Leu Pro Phe
                        420                 425                 430

Lys Arg Pro Leu Val Asp Ser Lys Gln Ala Ala Ala Asp Ser Lys Pro
                        435                 440                 445

Asn Lys Ser Lys Pro Lys Gly Asn Ala Ala
                        450                 455

<210> SEQ ID NO 21
<211> LENGTH: 2445
<212> TYPE: DNA
<213> ORGANISM: Zea mays

<400> SEQUENCE: 21
ggcgaccggc cagcgccata tcccgcgccg ccgccgccgc cgccgccgcc gccaacgctt      60
aatgctagtg ttcctccggc gaggcctctt gctcgtccgg cagcccacca cccgcgtcct     120
tgccaaaccg tctctccgcc ctgcttgtct cttcgtccac cacttcgccg tcgacacgat     180
gggtgagggt tctgctgctg gtaaggacgc gaaggggaag gggaagggga aggggaagac     240
caaggccgcc gccgcggatt cggccctggt cgttcgcgac gactcctacc tagaggcggt     300
cactcagaag aggattcgct tcttcgagga gatccaggca aggcaagccg tcgagcggct     360
gaatatcggc ggcgaagtta tcaaggtaac tttgcctgat ggcgctatca aggagggtaa     420
gaaatggata caacccccaa tggatattgc taagagagata tcaagtggat ttgcagctag     480
ttgtttgata gctcaagtgg acgaaacact ctgggacatg gggaggccac tcgaaggtga     540
ttgtaaattg caaatgttca gtttgatac caatgaaggt cgtgacacct tctggcactc     600
aagtgctcat attcttggag aatctattga gagagcatat ggatgcaagc tgtgtattgg     660
gccttgcacc acaagagggg agggtttcta ctatgatgct tactacaatg atcagacatt     720
gaatgaggag cactttggta tcattgaaaa ccaagctaaa aaggctgttg cggaaaagca     780
accgtttgaa cgcattgagg tcagcagggc agaagctctt gaaatgtttg ctgagaatga     840
attcaaggtt gaaatcatta atgagttgcc tgaggacaag accattactg tatacaggtg     900
tggtccttta gttgacctat gccgtgggcc acacatccca aatacttcct ttgtcaaagc     960
tttcgcttgt ctgaaggctt catcatcata ttggagagga aaagttgacc gcgaaagcct    1020
gcagagagta tatggaattt ctttccctga ttctcgacgt ctcacggaat ataaacattt    1080
tctagaggaa gctaagaaac gtgatcatag gatattagga aaagcacagg aactcttctt    1140
tttccatgaa cttagccctg gaagctgctt cttccttcca catggtgcca ggatatataa    1200
caaactgatg gacttcatgc gacaacagta cagagataga ggataccaag aggtgttgag    1260
cccaaatatt tacaatatgc aactatggga aacttctgga cacgccgcaa actataagga    1320
gaacatgttt gttttttgaga tcgagaaaca ggaatttgga cttaagccaa tgaattgtcc    1380
aggacactgt ctaatgtttg ctaatagggt tcggtcgtac agagagttgc ctcttcgcat    1440
ggctgatttt ggagtgcttc atagaaatga gcttagtggt gctcttacag gtttgacacg    1500
tgttagaaga ttccagcagg atgatgctca tatcttctgc agagaagacc aaatcaagga    1560
tgaagttaag gctgttttgg aattcatcaa ttatgtttat gagatatttg gcttcaaata    1620
tgagttggag ttgtctacga gaccagagaa gtatctaggt gaagttgaaa cttggaacaa    1680
agctgaacaa caattgacag aagctttaaa tgagtttggg aagccatgga agattaatga    1740 agggatggt gctttctacg gcccaaaaat tgatattggt gtgtttgatg cccttaagag    1800
```

```
gaaatttcag tgtgcaaccc tacagctgga ttttcagctg cccattcggt tcaagctggc   1860
ttattctgct gaggatgaag ccaaaattga aaggcctgtg atgatacaca gggcaatcct   1920
aggttcggtt gaaaggatgc ttgccattct tttggagcat acaatggta aatgccctt    1980 atggctaagc cctcgccagg ccattgtttg ctcggtatct tctggttcag tggaatatgc   2040
gaaacaggtt cttgccactc tacatgaagc tggttttcat gttgatattg acgcgagtga   2100
caggacaata caaagaagg tacgggaagc tcaactggcc caattcaact acattcttgt   2160
cgtaggtgca caagaggccg agactggaaa tatatgcgtt agggtaagag acaatgctga   2220
cctggtcaca acgagtgtag atggcttcat cacacgtttg agggacgaaa tcgcagcctt   2280
caaatgattt tgatgctgca taatttccta ctactcgttt gtgattttga cgagtttta    2340 gtgaccagca tcgagttcct cgtgttactg ttcttgtttg tatgaagcta aaaggttgtc   2400
tttttgttat taattacaga tgcgaagtta aatactgccg ctagt                  2445

<210> SEQ ID NO 22
<211> LENGTH: 741
<212> TYPE: PRT
<213> ORGANISM: Zea mays

<400> SEQUENCE: 22

Met Leu Val Phe Leu Arg Arg Gly Leu Leu Val Arg Gln Pro Thr
  1               5                  10                  15

Thr Arg Val Leu Ala Lys Pro Ser Leu Arg Pro Ala Cys Leu Phe Val
             20                  25                  30

His His Phe Ala Val Asp Thr Met Gly Glu Gly Ser Ala Ala Gly Lys
         35                  40                  45

Asp Ala Lys Gly Lys Gly Lys Gly Lys Lys Thr Lys Ala Ala Ala
     50                  55                  60

Ala Asp Ser Ala Leu Val Val Arg Asp Asp Ser Tyr Leu Glu Ala Val
 65                  70                  75                  80

Thr Gln Lys Arg Ile Arg Phe Glu Glu Ile Gln Ala Arg Gln Ala
                 85                  90                  95

Val Glu Arg Leu Asn Ile Gly Gly Glu Val Ile Lys Val Thr Leu Pro
            100                 105                 110

Asp Gly Ala Ile Lys Glu Gly Lys Lys Trp Ile Thr Thr Pro Met Asp
        115                 120                 125

Ile Ala Lys Glu Ile Ser Ser Gly Phe Ala Ala Ser Cys Leu Ile Ala
    130                 135                 140

Gln Val Asp Glu Thr Leu Trp Asp Met Gly Arg Pro Leu Glu Gly Asp
145                 150                 155                 160

Cys Lys Leu Gln Met Phe Lys Phe Asp Thr Asn Glu Gly Arg Asp Thr
                165                 170                 175

Phe Trp His Ser Ser Ala His Ile Leu Gly Glu Ser Ile Glu Arg Ala
            180                 185                 190

Tyr Gly Cys Lys Leu Cys Ile Gly Pro Cys Thr Thr Arg Gly Glu Gly
        195                 200                 205

Phe Tyr Tyr Asp Ala Tyr Tyr Asn Asp Gln Thr Leu Asn Glu Glu His
    210                 215                 220

Phe Gly Ile Ile Glu Asn Gln Ala Lys Ala Val Ala Glu Lys Gln
225                 230                 235                 240

Pro Phe Glu Arg Ile Glu Val Ser Arg Ala Glu Ala Leu Glu Met Phe
                245                 250                 255

Ala Glu Asn Glu Phe Lys Val Glu Ile Ile Asn Glu Leu Pro Glu Asp
```

-continued

```
                    260                 265                 270
Lys Thr Ile Thr Val Tyr Arg Cys Gly Pro Leu Val Asp Leu Cys Arg
            275                 280                 285
Gly Pro His Ile Pro Asn Thr Ser Phe Val Lys Ala Phe Ala Cys Leu
290                 295                 300
Lys Ala Ser Ser Ser Tyr Trp Arg Gly Lys Val Asp Arg Glu Ser Leu
305                 310                 315                 320
Gln Arg Val Tyr Gly Ile Ser Phe Pro Asp Ser Arg Arg Leu Thr Glu
                    325                 330                 335
Tyr Lys His Phe Leu Glu Ala Lys Lys Arg Asp His Arg Ile Leu
                340                 345                 350
Gly Lys Ala Gln Glu Leu Phe Phe His Glu Leu Ser Pro Gly Ser
            355                 360                 365
Cys Phe Phe Leu Pro His Gly Ala Arg Ile Tyr Asn Lys Leu Met Asp
370                 375                 380
Phe Met Arg Gln Gln Tyr Arg Asp Arg Gly Tyr Gln Glu Val Leu Ser
385                 390                 395                 400
Pro Asn Ile Tyr Asn Met Gln Leu Trp Glu Thr Ser Gly His Ala Ala
                    405                 410                 415
Asn Tyr Lys Glu Asn Met Phe Val Phe Glu Ile Glu Lys Gln Glu Phe
                420                 425                 430
Gly Leu Lys Pro Met Asn Cys Pro Gly His Cys Leu Met Phe Ala Asn
            435                 440                 445
Arg Val Arg Ser Tyr Arg Glu Leu Pro Leu Arg Met Ala Asp Phe Gly
        450                 455                 460
Val Leu His Arg Asn Glu Leu Ser Gly Ala Leu Thr Gly Leu Thr Arg
465                 470                 475                 480
Val Arg Arg Phe Gln Gln Asp Asp Ala His Ile Phe Cys Arg Glu Asp
                    485                 490                 495
Gln Ile Lys Asp Glu Val Lys Ala Val Leu Glu Phe Ile Asn Tyr Val
                500                 505                 510
Tyr Glu Ile Phe Gly Phe Lys Tyr Glu Leu Glu Leu Ser Thr Arg Pro
            515                 520                 525
Glu Lys Tyr Leu Gly Glu Val Glu Thr Trp Asn Lys Ala Glu Gln Gln
530                 535                 540
Leu Thr Glu Ala Leu Asn Glu Phe Gly Lys Pro Trp Lys Ile Asn Glu
545                 550                 555                 560
Gly Asp Gly Ala Phe Tyr Gly Pro Lys Ile Asp Ile Gly Val Phe Asp
                    565                 570                 575
Ala Leu Lys Arg Lys Phe Gln Cys Ala Thr Leu Gln Leu Asp Phe Gln
                580                 585                 590
Leu Pro Ile Arg Phe Lys Leu Ala Tyr Ser Ala Glu Asp Glu Ala Lys
            595                 600                 605
Ile Glu Arg Pro Val Met Ile His Arg Ala Ile Leu Gly Ser Val Glu
610                 615                 620
Arg Met Leu Ala Ile Leu Leu Glu His Tyr Asn Gly Lys Trp Pro Leu
625                 630                 635                 640
Trp Leu Ser Pro Arg Gln Ala Ile Val Cys Ser Val Ser Ser Gly Ser
                    645                 650                 655
Val Glu Tyr Ala Lys Gln Val Leu Ala Thr Leu His Glu Ala Gly Phe
                660                 665                 670
His Val Asp Ile Asp Ala Ser Asp Arg Thr Ile Gln Lys Lys Val Arg
            675                 680                 685
```

Glu Ala Gln Leu Ala Gln Phe Asn Tyr Ile Leu Val Val Gly Ala Gln
    690                 695                 700

Glu Ala Glu Thr Gly Asn Ile Cys Val Arg Val Arg Asp Asn Ala Asp
705                 710                 715                 720

Leu Val Thr Thr Ser Val Asp Gly Phe Ile Thr Arg Leu Arg Asp Glu
                725                 730                 735

Ile Ala Ala Phe Lys
            740

<210> SEQ ID NO 23
<211> LENGTH: 1758
<212> TYPE: DNA
<213> ORGANISM: Oryza sativa

<400> SEQUENCE: 23

| | | | | | |
|---|---|---|---|---|---|
| gcacgagatt | atgatgccta | ctacaatgat | ctgacattga | atgagacaca | ttttggtatc | 60 |
| attgatgccc | aagcacagaa | agctgttgcg | gaaaaacaac | catttgaacg | aattgaggtc | 120 |
| tccagggcag | aggcccttga | aatgttcgca | gaaataaat | ttaaggttga | aatcattaat | 180 |
| gagttgcctg | aagacaagac | cattacagta | tacagatgtg | gtcctctagt | tgacctttgc | 240 |
| cgtgggccac | acatccccaa | tacttccttt | gttaaagctt | ttgcttgtct | taaggcatca | 300 |
| tcgtcgtatt | ggagagggaa | agcagatcga | gagagcctgc | agagagtata | tggaatttct | 360 |
| tttcctgatt | ctaaacgtct | caaggaatat | aaacatctgc | tagaagaggc | taagaagcgt | 420 |
| gatcataggc | tattaggaca | gacccaggat | ctcttctttt | tccatcaact | tagtccagga | 480 |
| agctgcttct | tccttccaca | tggtgctata | atatacaaca | aattgatgga | ttttttgcga | 540 |
| cagcaataca | gagatagagg | atatcaagag | gttttgagcc | caaatatta | caatatgcaa | 600 |
| ctctgggaaa | cctctggaca | tgctgcaaac | tacaaggaga | atatgttgt | ttttgagatt | 660 |
| gagaaacagg | aatttggtct | caagccaatg | aattgtcctg | gccattgcct | aatgtttgag | 720 |
| cacaggggttc | gttcatacag | agaattgcct | ctccggatgg | ctgattttgg | agtccttcac | 780 |
| aggaatgagc | ttagtggtgc | acttacaggt | ttgacacgtg | ttagaagatt | ccagcaggat | 840 |
| gatgcccata | ttttttgcag | agaaagccaa | atcaaggacg | aagttaaggc | tgttttggac | 900 |
| ttcatcaatt | atgtttacga | gatatttgga | tttaaatatg | aattggagct | atcaacgaga | 960 |
| ccagaaaagt | acttaggtga | tattgaaacc | tggaacaaag | cagagcaaca | gctgacagaa | 1020 |
| gccttaaatg | agtttggaaa | gccatggcag | atcaatgaag | gtgatggtgc | cttctatggt | 1080 |
| ccaaaaattg | atattggtgt | gtttgatgcc | ctcaagagga | aatttcagtg | tgcaactcta | 1140 |
| cagctcgatt | ttcagctgcc | cctacgcttc | aagctgactt | actctgcaga | ggatgaagcc | 1200 |
| aaacttgaga | ggcctgtgat | gattcacagg | gcaatcctag | gttctgttga | aaggatgttt | 1260 |
| gctattcttt | tggagcatta | caatggtaaa | tggcccttgt | ggttgagtcc | tcgccaagcc | 1320 |
| attgtttgct | ccatatcttc | caattcagtg | gaatacgcta | acaggtccg | tgctaggata | 1380 |
| catgaagctg | gttttcatgt | agccatcgat | gagacagaca | ggacaataca | gaagaaggta | 1440 |
| cgggaggctc | aattagccca | attcaactac | attcttgtcg | ttggtgcaca | agaagcagag | 1500 |
| actggacagg | tcagcgtcag | ggtaagggac | aaagctgaac | tagccacagt | gagcattgat | 1560 |
| gacatcatca | cacgttttaa | ggaggaagta | gcagcttaca | aatgattttg | atttcacacc | 1620 |
| cttttgctaa | gaatttactc | caaatttgtg | attttgatgg | tgtagcgggc | agtgtaatct | 1680 |
| tgctatttta | tttcttgaca | aaagtacatc | tgattgtctt | ttcttaataa | cgaaagtgtg | 1740 |

-continued

```
ctattcttca tcagcgac                                              1758
```

<210> SEQ ID NO 24
<211> LENGTH: 530
<212> TYPE: PRT
<213> ORGANISM: Oryza sativa

<400> SEQUENCE: 24

| Tyr | Asp | Ala | Tyr | Tyr | Asn | Asp | Leu | Thr | Leu | Asn | Glu | Thr | His | Phe | Gly |
|---|---|---|---|---|---|---|---|---|---|---|---|---|---|---|---|
| 1 | | | | 5 | | | | | 10 | | | | | 15 | |

| Ile | Ile | Asp | Ala | Gln | Ala | Gln | Lys | Ala | Val | Ala | Glu | Lys | Gln | Pro | Phe |
| | | | 20 | | | | | 25 | | | | | 30 | | |

| Glu | Arg | Ile | Glu | Val | Ser | Arg | Ala | Glu | Ala | Leu | Glu | Met | Phe | Ala | Glu |
| | | 35 | | | | | 40 | | | | | 45 | | | |

| Asn | Lys | Phe | Lys | Val | Glu | Ile | Ile | Asn | Glu | Leu | Pro | Glu | Asp | Lys | Thr |
| | 50 | | | | | 55 | | | | | 60 | | | | |

| Ile | Thr | Val | Tyr | Arg | Cys | Gly | Pro | Leu | Val | Asp | Leu | Cys | Arg | Gly | Pro |
| 65 | | | | | 70 | | | | | 75 | | | | | 80 |

| His | Ile | Pro | Asn | Thr | Ser | Phe | Val | Lys | Ala | Phe | Ala | Cys | Leu | Lys | Ala |
| | | | | 85 | | | | | 90 | | | | | 95 | |

| Ser | Ser | Ser | Tyr | Trp | Arg | Gly | Lys | Ala | Asp | Arg | Glu | Ser | Leu | Gln | Arg |
| | | | 100 | | | | | 105 | | | | | 110 | | |

| Val | Tyr | Gly | Ile | Ser | Phe | Pro | Asp | Ser | Lys | Arg | Leu | Lys | Glu | Tyr | Lys |
| | | 115 | | | | | 120 | | | | | 125 | | | |

| His | Leu | Leu | Glu | Glu | Ala | Lys | Lys | Arg | Asp | His | Arg | Leu | Leu | Gly | Gln |
| | 130 | | | | | 135 | | | | | 140 | | | | |

| Thr | Gln | Asp | Leu | Phe | Phe | Phe | His | Gln | Leu | Ser | Pro | Gly | Ser | Cys | Phe |
| 145 | | | | | 150 | | | | | 155 | | | | | 160 |

| Phe | Leu | Pro | His | Gly | Ala | Ile | Ile | Tyr | Asn | Lys | Leu | Met | Asp | Phe | Leu |
| | | | | 165 | | | | | 170 | | | | | 175 | |

| Arg | Gln | Gln | Tyr | Arg | Asp | Arg | Gly | Tyr | Gln | Glu | Val | Leu | Ser | Pro | Asn |
| | | | 180 | | | | | 185 | | | | | 190 | | |

| Ile | Tyr | Asn | Met | Gln | Leu | Trp | Glu | Thr | Ser | Gly | His | Ala | Ala | Asn | Tyr |
| | | 195 | | | | | 200 | | | | | 205 | | | |

| Lys | Glu | Asn | Met | Phe | Val | Phe | Glu | Ile | Glu | Lys | Gln | Glu | Phe | Gly | Leu |
| | 210 | | | | | 215 | | | | | 220 | | | | |

| Lys | Pro | Met | Asn | Cys | Pro | Gly | His | Cys | Leu | Met | Phe | Glu | His | Arg | Val |
| 225 | | | | | 230 | | | | | 235 | | | | | 240 |

| Arg | Ser | Tyr | Arg | Glu | Leu | Pro | Leu | Arg | Met | Ala | Asp | Phe | Gly | Val | Leu |
| | | | | 245 | | | | | 250 | | | | | 255 | |

| His | Arg | Asn | Glu | Leu | Ser | Gly | Ala | Leu | Thr | Gly | Leu | Thr | Arg | Val | Arg |
| | | | 260 | | | | | 265 | | | | | 270 | | |

| Arg | Phe | Gln | Gln | Asp | Asp | Ala | His | Ile | Phe | Cys | Arg | Glu | Ser | Gln | Ile |
| | | 275 | | | | | 280 | | | | | 285 | | | |

| Lys | Asp | Glu | Val | Lys | Ala | Val | Leu | Asp | Phe | Ile | Asn | Tyr | Val | Tyr | Glu |
| | 290 | | | | | 295 | | | | | 300 | | | | |

| Ile | Phe | Gly | Phe | Lys | Tyr | Glu | Leu | Glu | Leu | Ser | Thr | Arg | Pro | Glu | Lys |
| 305 | | | | | 310 | | | | | 315 | | | | | 320 |

| Tyr | Leu | Gly | Asp | Ile | Glu | Thr | Trp | Asn | Lys | Ala | Glu | Gln | Gln | Leu | Thr |
| | | | | 325 | | | | | 330 | | | | | 335 | |

| Glu | Ala | Leu | Asn | Glu | Phe | Gly | Lys | Pro | Trp | Gln | Ile | Asn | Glu | Gly | Asp |
| | | | 340 | | | | | 345 | | | | | 350 | | |

| Gly | Ala | Phe | Tyr | Gly | Pro | Lys | Ile | Asp | Ile | Gly | Val | Phe | Asp | Ala | Leu |
| | | 355 | | | | | 360 | | | | | 365 | | | |

| | | | | | | | | | | | | | | |
|---|---|---|---|---|---|---|---|---|---|---|---|---|---|---|
| Lys | Arg | Lys | Phe | Gln | Cys | Ala | Thr | Leu | Gln | Leu | Asp | Phe | Gln | Leu | Pro |
| | 370 | | | | 375 | | | | | 380 | | | | | |
| Leu | Arg | Phe | Lys | Leu | Thr | Tyr | Ser | Ala | Glu | Asp | Glu | Ala | Lys | Leu | Glu |
| 385 | | | | | 390 | | | | | 395 | | | | | 400 |
| Arg | Pro | Val | Met | Ile | His | Arg | Ala | Ile | Leu | Gly | Ser | Val | Glu | Arg | Met |
| | | | | 405 | | | | | 410 | | | | | 415 | |
| Phe | Ala | Ile | Leu | Leu | Glu | His | Tyr | Asn | Gly | Lys | Trp | Pro | Leu | Trp | Leu |
| | | | | 420 | | | | | 425 | | | | | 430 | |
| Ser | Pro | Arg | Gln | Ala | Ile | Val | Cys | Ser | Ile | Ser | Ser | Asn | Ser | Val | Glu |
| | | | 435 | | | | | 440 | | | | | 445 | | |
| Tyr | Ala | Lys | Gln | Val | Arg | Ala | Arg | Ile | His | Glu | Ala | Gly | Phe | His | Val |
| | 450 | | | | | 455 | | | | | 460 | | | | |
| Ala | Ile | Asp | Glu | Thr | Asp | Arg | Thr | Ile | Gln | Lys | Lys | Val | Arg | Glu | Ala |
| 465 | | | | | 470 | | | | | 475 | | | | | 480 |
| Gln | Leu | Ala | Gln | Phe | Asn | Tyr | Ile | Leu | Val | Val | Gly | Ala | Gln | Glu | Ala |
| | | | | 485 | | | | | 490 | | | | | 495 | |
| Glu | Thr | Gly | Gln | Val | Ser | Val | Arg | Val | Arg | Asp | Lys | Ala | Glu | Leu | Ala |
| | | | 500 | | | | | 505 | | | | | 510 | | |
| Thr | Val | Ser | Ile | Asp | Asp | Ile | Ile | Thr | Arg | Phe | Lys | Glu | Glu | Val | Ala |
| | 515 | | | | | 520 | | | | | 525 | | | | |
| Ala | Tyr | | | | | | | | | | | | | | |
| | 530 | | | | | | | | | | | | | | |

<210> SEQ ID NO 25
<211> LENGTH: 2380
<212> TYPE: DNA
<213> ORGANISM: Glycine max

<400> SEQUENCE: 25

```
gcacgagaca ctatgctatg ctatgctctc taatccgttt ccgccgttac gctccttcct      60
accgcactct ccactctctc tttccgacga ttaaccgttt ctcctcctcc gtctcctccg     120
cctccgccgc catggttgct cacgcgaagg acgaggcgta cctcagcgcg acgattccga     180
aacgcatccg tctcttcgag accatcctgg cggagcagca cactcagcgc ctctcgctct     240
ccccggatcc tatcaaggtt actctccccg acggcagcgt caaggaggcg aagaagtggc     300
atacgacgcc gcttgatgtt gcgcgtgaaa tctcgaagaa tttggccaac agcgcgctca     360
cgcgaaggt caatggcgtg ctctgggaca tgactcgccc ctcgaggac gattgccagc     420
tccagatctt caagttcgac gacgacgaag gccgcgacac cttctggcac tccagcgccc     480
acattctcgg ccagtcactt gagacggagt atggatgcaa gctctgcatt gggccttgca     540
ctacaagagg agagggattc tattatgatg catttacgg ggagttgggt ctcaatgacg     600
atcactttaa gcagattgag gctggagcat tgaaggctgt tgcggaaaag caacccttg     660
agcgtattga agttacacgt gatcaggcac ttgagatgtt tcagataat aagtttaagg     720
ttgagattat caatgatttg cctgccgaca aaactatcac agtatacaga tgtggcccct     780
tggttgattt gtgtcgtgga ccccatatac ctaatacatc ctttgtcaaa gcaattgcgt     840
gcttaaaggc ttcatcagca tattggaggg gggacaaaga tcgggaaagt ttacaaagag     900
tttatggcat atcttatcct gatcagaaaa gtctaaagga atacttgcat cggctggagg     960
aggctaaaaa gtatgatcac aggattttgg gtgtgaaaca ggagcttatt cttcatcatg    1020
aatggagccc gggaagctgg ttttttcttc cgcaaggcac tcggatctac aacaaactca    1080
tggacttcat tcggaatcag tacagagaca ggggctatca agaggtcata tctcccaatg    1140
```

-continued

```
tatttaacat ggaactgtgg gtgcaatctg gtcatgctgc aaattatagg gaggatatgt   1200
ttatcttaga ggttgacaaa caagagtttg ggttgaaacc aatgaattgc ccagggcact   1260
gcctgatgtt taaacacagg gttcgatcat atagagaact tcctcttcgt ttcgctgatt   1320
ttggggtttt gcatcggaat gaggctagtg gcgccctgag tggattaaca cgtgttagga   1380
gattccagca ggacgatgca catatttct gcagggagtc ccagataaag gatgaagtga    1440
ggaacagctt gaatttcatc aattatgtct ataagatatt tggtttcaca tatgagctga   1500
agctttcaac gaggccagaa aaataccag gagatattgc aacttgggac aaagctgaaa    1560
gtgctcttaa agaagcttta gatgattttg gcaagccttg gcagttgaat gaaggggatg   1620
gtgcattcta tggaccaaag atagacatca gtgtatctga tgcattgggt aggaaattcc   1680
agtgtgcaac tttgcagctt gacttccagc ttcctgatcg ttttaagttg gaattctcag   1740
ctgaggatga agccaaaatt gagagacctg taatgataca cagagccatt ctaggatctg   1800
ttgaacgcat gtttgccata cttttagagc actacaaggg taaatggcct ttctggctca   1860
gtcctcgtca agcaattgta tgccctgtgt ctgaaaagtc acaagcttat gcattacagg   1920
tgcgagatca gatccaccaa gcagggtatt acgttgatgc tgatacaact gataggaaga   1980
ttcaaaagaa ggtgcgagaa gcacaattag cacaatacaa ctacatcttg gttgttggag   2040
aggaggaagc taatacagga caggtgagtg tacgagttag agacttggca gaacataagg   2100
ttatgagtat tgagaagcta cttgaacatt tcagagacaa agctgcagct ttcgaatgat   2160
actttgcatg tgaaaactgt cgaagaaaat tttcagcccc aaataccttg gttttacaca   2220
gttgtgtgcg catttgatt ttcaacttaa gcaattatc ctgatttat ttatgatttg      2280
aatgatcact gtatttcgca ctagaaacat aatgtgaatc ttggtcatac ctggagcgca   2340
ctctggttga tctttatatc aaaaaaaaaa aaaaaaaaa                          2380
```

<210> SEQ ID NO 26
<211> LENGTH: 698
<212> TYPE: PRT
<213> ORGANISM: Glycine max

<400> SEQUENCE: 26

```
Tyr Arg Thr Leu His Ser Leu Phe Pro Thr Ile Asn Arg Phe Ser Ser
  1               5                  10                  15

Ser Val Ser Ser Ala Ser Ala Ala Met Val Ala His Ala Lys Asp Glu
                 20                  25                  30

Ala Tyr Leu Ser Ala Thr Ile Pro Lys Arg Ile Arg Leu Phe Glu Thr
             35                  40                  45

Ile Leu Ala Glu Gln His Thr Gln Arg Leu Ser Leu Ser Pro Asp Pro
         50                  55                  60

Ile Lys Val Thr Leu Pro Asp Gly Ser Val Lys Glu Ala Lys Lys Trp
 65                  70                  75                  80

His Thr Thr Pro Leu Asp Val Ala Arg Glu Ile Ser Lys Asn Leu Ala
                 85                  90                  95

Asn Ser Ala Leu Ile Ala Lys Val Asn Gly Val Leu Trp Asp Met Thr
            100                 105                 110

Arg Pro Leu Glu Asp Asp Cys Gln Leu Gln Ile Phe Lys Phe Asp Asp
        115                 120                 125

Asp Glu Gly Arg Asp Thr Phe Trp His Ser Ser Ala His Ile Leu Gly
    130                 135                 140

Gln Ser Leu Glu Thr Glu Tyr Gly Cys Lys Leu Cys Ile Gly Pro Cys
145                 150                 155                 160
```

-continued

```
Thr Thr Arg Gly Glu Gly Phe Tyr Tyr Asp Ala Phe Tyr Gly Glu Leu
            165                 170                 175
Gly Leu Asn Asp Asp His Phe Lys Gln Ile Glu Ala Gly Ala Leu Lys
        180                 185                 190
Ala Val Ala Glu Lys Gln Pro Phe Glu Arg Ile Glu Val Thr Arg Asp
    195                 200                 205
Gln Ala Leu Glu Met Phe Ser Asp Asn Lys Phe Lys Val Glu Ile Ile
    210                 215                 220
Asn Asp Leu Pro Ala Asp Lys Thr Ile Thr Val Tyr Arg Cys Gly Pro
225                 230                 235                 240
Leu Val Asp Leu Cys Arg Gly Pro His Ile Pro Asn Thr Ser Phe Val
                245                 250                 255
Lys Ala Ile Ala Cys Leu Lys Ala Ser Ser Ala Tyr Trp Arg Gly Asp
                260                 265                 270
Lys Asp Arg Glu Ser Leu Gln Arg Val Tyr Gly Ile Ser Tyr Pro Asp
            275                 280                 285
Gln Lys Ser Leu Lys Glu Tyr Leu His Arg Leu Glu Glu Ala Lys Lys
        290                 295                 300
Tyr Asp His Arg Ile Leu Gly Val Lys Gln Glu Leu Ile Leu His His
305                 310                 315                 320
Glu Trp Ser Pro Gly Ser Trp Phe Phe Leu Pro Gln Gly Thr Arg Ile
                325                 330                 335
Tyr Asn Lys Leu Met Asp Phe Ile Arg Asn Gln Tyr Arg Asp Arg Gly
            340                 345                 350
Tyr Gln Glu Val Ile Ser Pro Asn Val Phe Asn Met Glu Leu Trp Val
        355                 360                 365
Gln Ser Gly His Ala Ala Asn Tyr Arg Glu Asp Met Phe Ile Leu Glu
    370                 375                 380
Val Asp Lys Gln Glu Phe Gly Leu Lys Pro Met Asn Cys Pro Gly His
385                 390                 395                 400
Cys Leu Met Phe Lys His Arg Val Arg Ser Tyr Arg Glu Leu Pro Leu
                405                 410                 415
Arg Phe Ala Asp Phe Gly Val Leu His Arg Asn Glu Ala Ser Gly Ala
                420                 425                 430
Leu Ser Gly Leu Thr Arg Val Arg Arg Phe Gln Gln Asp Asp Ala His
            435                 440                 445
Ile Phe Cys Arg Glu Ser Gln Ile Lys Asp Glu Val Arg Asn Ser Leu
        450                 455                 460
Asn Phe Ile Asn Tyr Val Tyr Lys Ile Phe Gly Phe Thr Tyr Glu Leu
465                 470                 475                 480
Lys Leu Ser Thr Arg Pro Glu Lys Tyr Leu Gly Asp Ile Ala Thr Trp
                485                 490                 495
Asp Lys Ala Glu Ser Ala Leu Lys Glu Ala Leu Asp Asp Phe Gly Lys
            500                 505                 510
Pro Trp Gln Leu Asn Glu Gly Asp Gly Ala Phe Tyr Gly Pro Lys Ile
        515                 520                 525
Asp Ile Ser Val Ser Asp Ala Leu Gly Arg Lys Phe Gln Cys Ala Thr
    530                 535                 540
Leu Gln Leu Asp Phe Gln Leu Pro Asp Arg Phe Lys Leu Glu Phe Ser
545                 550                 555                 560
Ala Glu Asp Glu Ala Lys Ile Glu Arg Pro Val Met Ile His Arg Ala
                565                 570                 575
```

```
Ile Leu Gly Ser Val Glu Arg Met Phe Ala Ile Leu Glu His Tyr
            580                 585                 590

Lys Gly Lys Trp Pro Phe Trp Leu Ser Pro Arg Gln Ala Ile Val Cys
        595                 600                 605

Pro Val Ser Glu Lys Ser Gln Ala Tyr Ala Leu Gln Val Arg Asp Gln
    610                 615                 620

Ile His Gln Ala Gly Tyr Tyr Val Asp Ala Asp Thr Thr Asp Arg Lys
625                 630                 635                 640

Ile Gln Lys Lys Val Arg Glu Ala Gln Leu Ala Gln Tyr Asn Tyr Ile
                645                 650                 655

Leu Val Val Gly Glu Glu Ala Asn Thr Gly Gln Val Ser Val Arg
            660                 665                 670

Val Arg Asp Leu Ala Glu His Lys Val Met Ser Ile Glu Lys Leu Leu
        675                 680                 685

Glu His Phe Arg Asp Lys Ala Ala Ala Phe
    690                 695

<210> SEQ ID NO 27
<211> LENGTH: 1677
<212> TYPE: DNA
<213> ORGANISM: Triticum aestivum

<400> SEQUENCE: 27
cggaaaatga atttaaggtt gaataatta acgaattgcc cgaggacaag accattacag      60
tatacagatg tggtcctttg gtcgacctct gccgtggccc gcacatccca aatacttcct     120
ttgttaaagc tttcgcttgc ctcaaggctt cagcatcata ctggagagga aaagcagacc    180
gtgagagcct gcagagagta tatggaatct ccttccctga ttctaaacgt ctcaaggaat    240
atcaacatat gatagaggaa gctaagaaac gcgatcatag gttactaggg cagtcccaga    300
aactcttctt tttccatcca cttagcccag gtagctgctt cttccttcca aatggcgcta    360
taatatataa caaattgatg gatttttttgc gcaaggagta tagagagaga ggctaccaag    420
aggttctgag tccaaatatt tacaacatgc aactttggga acctctgga catgctgcaa     480 actacaagga caacatgttt gttttgaga tcgagaaaca agaatttggc cttaagccaa      540
tgaattgtcc tggccattgc ctaatgtttg gacacgaggt tcgatcgtat agagagttgc    600
ctctccgcat ggctgatttt ggagttctgc acagaaatga acttagtggt gcacttacag    660
gtttgacacg tgtcagaaga ttccaacagg acgatgccca tattttttgc atggagagcc    720
aaatcaagga tgaagttcgg gcttgcttgg agttcattga ttatgtttat aaaatatttg    780
ggtttgaata tgagctggag ttatcaacga ccagagaa gtatttaggt gacattgaga      840
cctggaacaa agcagagcaa caactgacag aagcattgaa tgagtttggg aagccatgga    900
agataaatga agcagatggt gctttctatg gcccgaaaat agatattggt gtgtttgatg     960
ccctcaagag gaaatttcag tgtgcaactc tacagctcga ttttcagctg ccacttcgct    1020
tcaagttgac ttattctgca gaggatgaag ccaagcttga gaggcctgta atgatacaca    1080
gggcaatact aggatcagtt gaaaggatgt tgccattct tttggagcac tataatggta    1140
aatggccgtt gtggttaagc ccccgacaag ccattgtttg ctgtgtatct gccaattcac    1200
taacatatgc aaaagaggtt catgctcaga tacgtgcagc tggttttcat gttgacattg    1260
acatgactga tagaacaatt caaagaagg tgcgggaggc tcagttagcc caattcaact    1320
atattctagt cgtcggcgca aaagaggcag agtctgaaa ggtctctctg agggtaagag    1380
acagggcaga cctatccaca gagagcattg ctgacgtcat tgcacgtttt aacgacgaag    1440
```

```
ttgcgtcttt ccagtgattt ttaagtcgca tcatctttt tttgtccaag acatctactg    1500
cacaacccac attgtaattt ggtgaagtga ggtgaatgaa aaatcatgat attcttgttc    1560
atgttgtcac atgtacatta actgccatga tgtatcaatt ctataagggc ctctttgatt    1620
cgaaggattt tcatggggat tggaaaaaaa aaaaaaaaaa aaaaaaaaaa aaaaaaa       1677
```

<210> SEQ ID NO 28
<211> LENGTH: 483
<212> TYPE: PRT
<213> ORGANISM: Triticum aestivum

<400> SEQUENCE: 28

```
Glu Asn Glu Phe Lys Val Glu Ile Ile Asn Glu Leu Pro Glu Asp Lys
 1               5                  10                  15

Thr Ile Thr Val Tyr Arg Cys Gly Pro Leu Val Asp Leu Cys Arg Gly
             20                  25                  30

Pro His Ile Pro Asn Thr Ser Phe Val Lys Ala Phe Ala Cys Leu Lys
         35                  40                  45

Ala Ser Ala Ser Tyr Trp Arg Gly Lys Ala Asp Arg Glu Ser Leu Gln
     50                  55                  60

Arg Val Tyr Gly Ile Ser Phe Pro Asp Ser Lys Arg Leu Lys Glu Tyr
 65                  70                  75                  80

Gln His Met Ile Glu Glu Ala Lys Lys Arg Asp His Arg Leu Leu Gly
                 85                  90                  95

Gln Ser Gln Lys Leu Phe Phe His Pro Leu Ser Pro Gly Ser Cys
            100                 105                 110

Phe Phe Leu Pro Asn Gly Ala Ile Ile Tyr Asn Lys Leu Met Asp Phe
        115                 120                 125

Leu Arg Lys Glu Tyr Arg Glu Arg Gly Tyr Gln Glu Val Leu Ser Pro
    130                 135                 140

Asn Ile Tyr Asn Met Gln Leu Trp Glu Thr Ser Gly His Ala Ala Asn
145                 150                 155                 160

Tyr Lys Asp Asn Met Phe Val Phe Glu Ile Glu Lys Gln Glu Phe Gly
                165                 170                 175

Leu Lys Pro Met Asn Cys Pro Gly His Cys Leu Met Phe Gly His Glu
            180                 185                 190

Val Arg Ser Tyr Arg Glu Leu Pro Leu Arg Met Ala Asp Phe Gly Val
        195                 200                 205

Leu His Arg Asn Glu Leu Ser Gly Ala Leu Thr Gly Leu Thr Arg Val
    210                 215                 220

Arg Arg Phe Gln Gln Asp Asp Ala His Ile Phe Cys Met Glu Ser Gln
225                 230                 235                 240

Ile Lys Asp Glu Val Arg Ala Cys Leu Glu Phe Ile Asp Tyr Val Tyr
                245                 250                 255

Lys Ile Phe Gly Phe Glu Tyr Glu Leu Glu Leu Ser Thr Arg Pro Glu
            260                 265                 270

Lys Tyr Leu Gly Asp Ile Glu Thr Trp Asn Lys Ala Glu Gln Gln Leu
        275                 280                 285

Thr Glu Ala Leu Asn Glu Phe Gly Lys Pro Trp Lys Ile Asn Glu Ala
    290                 295                 300

Asp Gly Ala Phe Tyr Gly Pro Lys Ile Asp Ile Gly Val Phe Asp Ala
305                 310                 315                 320

Leu Lys Arg Lys Phe Gln Cys Ala Thr Leu Gln Leu Asp Phe Gln Leu
                325                 330                 335
```

−continued

```
Pro Leu Arg Phe Lys Leu Thr Tyr Ser Ala Glu Asp Glu Ala Lys Leu
            340             345             350

Glu Arg Pro Val Met Ile His Arg Ala Ile Leu Gly Ser Val Glu Arg
        355             360             365

Met Phe Ala Ile Leu Leu Glu His Tyr Asn Gly Lys Trp Pro Leu Trp
    370             375             380

Leu Ser Pro Arg Gln Ala Ile Val Cys Cys Val Ser Ala Asn Ser Leu
385             390             395                         400

Thr Tyr Ala Lys Glu Val His Ala Gln Ile Arg Ala Ala Gly Phe His
            405             410             415

Val Asp Ile Asp Met Thr Asp Arg Thr Ile Gln Lys Lys Val Arg Glu
            420             425             430

Ala Gln Leu Ala Gln Phe Asn Tyr Ile Leu Val Val Gly Ala Lys Glu
        435             440             445

Ala Glu Ser Gly Lys Val Ser Leu Arg Val Arg Asp Arg Ala Asp Leu
    450             455             460

Ser Thr Glu Ser Ile Ala Asp Val Ile Ala Arg Phe Asn Asp Glu Val
465             470             475             480

Ala Ser Phe
```